United States Patent [19]

Gallatin et al.

[11] Patent Number: 5,437,958
[45] Date of Patent: Aug. 1, 1995

[54] HUMAN $\beta_2$ INTEGRIN $\alpha$ SUBUNIT

[75] Inventors: William M. Gallatin, Mercer Island; Monica Van der Vieren, Seattle, both of Wash.

[73] Assignee: ICOS Corporation, Bothell, Wash.

[21] Appl. No.: 173,497

[22] Filed: Dec. 23, 1993

[51] Int. Cl.$^6$ .................. C12N 5/00; C12P 21/06; C07H 19/00; C07K 1/00

[52] U.S. Cl. ..................... 435/240.2; 435/69.1; 435/252.3; 530/350; 536/22.1; 536/23.1; 536/23.5

[58] Field of Search ............... 435/69.1, 240.2, 252.3; 530/350; 536/22.1, 23.1, 23.5

[56] References Cited

PUBLICATIONS

Arfors, et al., "A monoclonal antibody to the membrane glycoprotein complex CD18 inhibits polymorphnuclear leukocyte accumulation and plasma leakage in vivo," *Blood* 69:338–340 (1987).
Arnaout, "Structure and function of the leukocyte adhesion moleucles CD11/CD18," *Blood* 75:1037–1050 (1990).
Burnett, et al., "The IgA heavy–chain gene family in rabbits: cloning and sequence analysis of 13 C$\alpha$ genes," *EMBO J.* 8:4041–4047 (1989).
Corbi, et al., "cDNA cloning and complete primary structure of the $\alpha$ subunit of a leukocyte adhesion glycoprotein, pp. 150, 95," *EMBO J.* 6:4023–4028 (1987).
Corbi, et al., "The human leukocyte adhesion glycoprotein Mac-1 (complement respector type 3, (CD11b) $\alpha$ subunit," *J. Biol. Chem.* 263:12403–12411 (1988).
Danilenko, et al., "Canine leukocyte cell adhesion molecules (LeuCAMS): characterization of the CD11/CD18 family," *Tissue Antigens* 40:13–21 (1992).
Greve, et al., "The major human rhinovirus receptor is ICAM-1," *Cell* 56:839 (1989).
Capecchi, "Altering the genome by homologous recombination," *Science* 244:1288–1292 (1989).
Karin and Richards, "Human metalothionein genes—primary structure of the metalothionein–II gene and a realted processed protein," *Nature* 299:797–802 (1982).
Kishimoto, et al., "Heterologous mutations in the $\beta$ subunit common to the LFA-1, Mac-1, and p. 1150,95 Glycoproteins cause leukocyte adhesion deficiency," *Cell* 50:193–202 (1987).
Kishimoto, et al., "Cloning of the $\beta$ subunit of the leukocyte adhesion proteins: homology to an extracelluar matrix receptor defines a novel supergene family," *Cell* 48:681–690 (1987).
Larson, et al., "Primary structure of the leukocyte function–associated moleucle-1 $\alpha$ subunit: an integrin with an embedded domain defining a protein superfamily," *J. Cell. Biol.* 108:703–712 (1989).
Larson and Springer, "Structure and function of leukocyte integrins," *Immunol. Rev.* 114:181–217 (1990).
Letvin, et al., "Conservation of myeloid surface antigens on primary granulocytes," *Blood* 61:408–410 (1983).
Metlay, et al., "The distinct leukocyte integrins of mouse spleen dendritic cells as identified with new hamster monoclonal antibodies," *J. Exp. Med.* 171:1753–1771 (1990).
Moore, et al., "Canine leukocyte integrins: characterization of a CD18 homologue," *Tissue Antigens* 36:211–220 (1990).
Nourshargh, et al., "Accumulation of $^{111}$In–neutrophils in rabbit skin in allergic and non-allergic inflammatory reactions in vivo," *J. Immunol.* 142:3193–3198 (1989).
Patarroyo, et al., "Leukocyte-cell adhesion: a molecu- (List continued on next page.)

*Primary Examiner*—Robert A. Wax
*Assistant Examiner*—Hyosuk Kim
*Attorney, Agent, or Firm*—Marshall, O'Toole, Gerstein, Murray & Borun

[57] ABSTRACT

DNA encoding a novel human $\beta_2$ integrin $\alpha$ subunit polypeptide, designated $\alpha_d$, is disclosed along with methods and materials for production of the same by recombinant procedures. Binding molecules specific for $\alpha_d$ are also disclosed as useful for modulating the biological activities of $\alpha_d$.

9 Claims, 4 Drawing Sheets

PUBLICATIONS lar process fundamental in leukocyte physiology," *Immunol. Rev.* 114:67–108 (1990).

Price, et al., "In vivo inhibition of neutrophil function in the rabbit using monoclonal antibody to CD18," *J. Immunol.* 139:4174–4177 (1987).

Sanchez-Madrid, et al., "A human leukocyte differentiation antigen family with distinct α-subunits and a common β-subunit," *J. Exp. Med.* 154:1517 (1981).

Schneiderman, et al., "Expression of 12 rabbit IgA $C_\alpha$ genes as chimeric rabbit-mouse IgA antibodies," *Proc. Natl. Acad. Sci. (USA)* 86:7562–7565 (1989).

Searle, et al., "Regulation linkage, and sequence of mouse metalothionein I and II genes," *Mol. Cell. Biol.* 4:1221–1230 (1984).

Smith, et al., "Cooperative interactions of LFA-1 and Mac-1 with intercellular adhesion molecule-1 in facilitating adherence and transendothelial migration of human neutrophils in vitro," *J. Clin. Invest.* 83:2008–2017 (1989).

Springer, "Adhesion moleucles of the immune system" *Nature* 346:425–434 (1990).

Tamura, et al., "Epithelial integrin$\alpha_6\beta^4$: complete primary structure of$\alpha^6$ and variant forms of $\beta^4$," *J. Cell. Biol.* 111:1593–1604 (1990).

Varsheny, et al., "Structure, organization, and regulation of human metalothionein $I^F$ gene: differential and cell-type-specific expression in response to heavy metals and glucocorticoids," *Mol. Cell Biol.* 6:26–36 (1986).

Vazeux et al. "Cloning and Characterization . . ." *Nature* 360: 485–488 Dec. 3, 1992.

```
αD     TF-GT--VLL  LSVLASYHGF  NLDVEEPTIF  QEDAGGFGQS  VVQFGGSRLV   47
CD11b  MA-LR--VLL  LTALTLCHGF  NLDTENAMTF  QENARGFGQS  VVQLQGSRVV   47
CD11c  MTRTRAALLL  FTALATSLGF  NLDTEELTAF  RVDSAGFGDS  VVQYANSWVV   50

αD     VGAPLEVVAA  NQTGRLYDCA  AATGMCQPIP  LHIRPEAVNM  SLGLTLAAST   97
CD11b  VGAPQEIVAA  NQRGSLYQCD  YSTGSCEPIR  LQVPVEAVNM  SLGLSLAATT   97
CD11c  VGAPQKIIAA  NQIGGLYQCG  YSTGACEPIG  LQVPPEAVNM  SLGLSLASTT  100

αD     NGSRLLACGP  TLHRVCGENS  YSKGSCLLLG  SR-WEIIQTV  PDATPECPHQ  146
CD11b  SPPQLLACGP  TVHQTCSENT  YVKGLCFLFG  SNLRQQPQKF  PEALRGCPQE  147
CD11c  SPSQLLACGP  TVHHECGRNM  YLTGLCFLLG  PT--QLTQRL  PVSRQECPRQ  148

αD     EMDIVFLIDG  SGSIDQNDFN  QMKGFVQAVM  GQFEGTDTLF  ALMQYSNLLK  196
CD11b  DSDIAFLIDG  SGSIIPHDFR  RMKEFVSTVM  EQLKKSKTLF  SLMQYSEEFR  197
CD11c  EQDIVFLIDG  SGSISSRNFA  TMMNFVRAVI  SQFQRPSTQF  SLMQFSNKFQ  198

αD     IHFTFTQFRT  SPSQQSLVDP  IVQLKGLTFT  ATGILTVVTQ  LFHHKNGARK  246
CD11b  IHFTFKEFQN  NPNPRSLVKP  ITQLLGRTHT  ATGIRKVVRE  LFNITNGARK  247
CD11c  THFTFEEFRR  TSNPLSLLAS  VHQLQGFTYT  ATAIQNVVHR  LFHASYGARR  248

αD     SAKKILIVIT  DGQKYKDPLE  YSDVIPQAEK  AGIIRYAIGV  GHAFQGPTAR  296
CD11b  NAFKILVVIT  DGEKFGDPLG  YEDVIPEADR  EGVIRYVIGV  GDAFRSEKSR  297
CD11c  DAIKILIVIT  DGKKEGDSLD  YKDVIPMADA  AGIIRYAIGV  GLAFQNRNSW  298
```

FIGURE 1A

```
αD     QELNTISSAP  PQDHVFKVDN  FAALGSIQKQ  LQEKIYAVEG  TQSRASSSFQ  346
CD11B  QELNTIASKP  PRDHVFQVNN  FEALKTIQNQ  LREKIFAIEG  TQTGSSSSFE  347
CD11C  KELNDIASKP  SQEHIFKVED  FDALKDIQNQ  LKEKIFAIEG  TETISSSSFE  348

αD     HEMSQEGFST  ALTMDGLFLG  AVGSFSWSGG  AFLYPPNMSP  TFINMSQENV  396
CD11B  HEMSQEGFSA  AITSNGPLLS  TVGSYDWAGG  VFLYTSKEKS  TFINMTRVDS  397
CD11C  LEMAQEGFSA  VFTPDGPVLG  AVGSFTWSGG  AFLYPPNMSP  TFINMSQENV  398

αD     DMRDSYLGYS  TELALWKGVQ  NLVLGAPRYQ  HTGKAVIFTQ  VSRQWRKKAE  446
CD11B  DMNDAYLGYA  AAIILRNRVQ  SLVLGAPRYQ  HIGLVAMFRQ  NTGMWESNAN  447
CD11C  DMRDSYLGYS  TELALWKGVQ  SLVLGAPRYQ  HIGKAVIFIQ  VSRQWRMKAE  448

αD     VTGTQIGSYF  GASLCSVDVD  SDGSTDLILI  GAPHYYEQTR  GGQVSVCPLP  496
CD11B  VKGTQIGAYF  GASLCSVDVD  SNGSTDLVLI  GAPHYYEQTR  GGQVSVCPLP  497
CD11C  VIGTQIGSYF  GASLCSVDVD  TDGSTDLVLI  GAPHYYEQTR  GGQVSVCPLP  498

αD     RGQRVQWQCD  AVLRGEQGHP  WGRFGAALTV  LGDVNEDKLI  DVAIGAPGEQ  546
CD11B  RGQRARWQCD  AVLYGEQGQP  WGRFGAALTV  LGDVNGDKLT  DVAIGAPGEE  547
CD11C  RGWRRWW-CD  AVLYGEQGHP  WGRFGAALTV  LGDVNGDKLT  DVVIGAPGEE  547

αD     ENRGAVYLFH  GASESGISPS  HSQRIASSQL  SPRLQYFGQA  LSGGQDLTQD  596
CD11B  DNRGAVYLFH  GTSGSGISPS  HSQRIAGSKL  SPRLQYFGQS  LSGGQDLTMD  597
CD11C  ENRGAVYLFH  GVLGPSISPS  HSQRIAGSQL  SSRLQYFGQA  LSGGQDLTQD  597
```

FIGURE 1B

| | | | | | |
|---|---|---|---|---|---|
| αD    | GLMDLAVGAR  | GQVLLLRSLP  | VLKVGVAMRF  | SPVEVAKAVY  | RCWEEKPSAL  | 646 |
| CD11B | GLVDLTVGAQ  | GHVLLLLRSQP | VLRVKAIMEF  | NPREVARNVF  | ECNDQVVKGK  | 647 |
| CD11C | GLVDLAVGAR  | GQVLLLRTRP  | VLWVGVSMQF  | IPAEIPRSAF  | ECREQVVSEQ  | 647 |

| | | | | | |
|---|---|---|---|---|---|
| αD    | EAGDATVCLT  | IQKSSLDQL-  | -GDIQSSVRF  | DLALDPGRLT  | SRAIFNETKN  | 694 |
| CD11B | EAGEVRVCLH  | VQKSTRDRLR  | EGQIQSVVTY  | DLALDSGRPH  | SRAVFNETKN  | 697 |
| CD11C | TLVQSNICLY  | IDKRSKNLLG  | SRDLQSSVTL  | DLALAPGRLS  | PRAIFQETKN  | 697 |

| | | | | | |
|---|---|---|---|---|---|
| αD    | PTLTTRKTLG  | LGIHCETLKL  | LLPDCVEDVV  | SPIILHLNFS  | LVREPIPSPQ  | 744 |
| CD11B | STRRQTQVLG  | LTQTCETLKL  | QLPNCIEDPV  | SPIVLRLNFS  | LVGTPLSAFG  | 747 |
| CD11C | RSLSRVRVLG  | LKAHCENFNL  | LLPSCVEDSV  | IPIILRLNFT  | LVGKPLLAFR  | 747 |

| | | | | | |
|---|---|---|---|---|---|
| αD    | NLRPVLAVGS  | QDLFTASLPF  | EKNCGQDGLC  | EGDLGVTLSF  | SGLQTLTVGS  | 794 |
| CD11B | NLRPVLAEDA  | QRLFTALFPF  | EKNCGNDNIC  | QDDLSITFSF  | MSLDCLVVGG  | 797 |
| CD11C | NLRPMLAALA  | QRYFTASLPF  | EKNCGADHIC  | QDNLGISFSF  | PGLKSLLVGS  | 797 |

| | | | | | |
|---|---|---|---|---|---|
| αD    | SLELNVIVTV  | WNAGEDSYGT  | VVSLYYPAGL  | SHRRVSGAQK  | QPHQSALRLA  | 844 |
| CD11B | PREFNVTVTV  | RNDGEDSYRT  | QVTFFFPLDL  | SYRKVSTLQN  | QRSQRSWRLA  | 847 |
| CD11C | NLELNAEVMV  | WNDGEDSYGT  | TITFSHPAGL  | SYRYVAEGQK  | QGQLRSLHLT  | 847 |

| | | | | | |
|---|---|---|---|---|---|
| αD    | CETVPTED--  | EGLRSSRCSV  | NHPIFHEGSN  | GTFIVTFDVS  | Y---KATLG   | 888 |
| CD11B | CESASSTEVS  | GALKSTSCSI  | NHPIFPENSE  | ----VTFNIT  | FDVDSKASLG  | 893 |
| CD11C | CCSA-PVGSQ  | GTW-STSCRI  | NHLIFRGGAQ  | ----ITFLAT  | FDVSPKAVGL  | 891 |

FIGURE 1C

|   |   |   |   |   |   |
|---|---|---|---|---|---|
| αD    | DRMLMRASAS | SENNKASSSK | ATFQLELPVK | YAVYTMISRQ | EESTKYFNFA | 938 |
| CD11B | NKLLLKANVT | SENNMPRTNK | TEFQLELPVK | YAVYMVVTSH | GVSTKYLNFT | 943 |
| CD11C | DRLLLIANVS | SENNIPRTSK | TIFQLELPVK | YAVYIVVSSH | EQFTKYLNFS | 941 |
|       |            |            |            |            |            |     |
| αD    | TS-DEKKMKE | AEHRYRVNNL | SQRDLAISIN | FWVPVLLNGV | AVWDVVMEAP | 987 |
| CD11B | AS-ENTS-RV | MQHQYQVSNL | GQRSLPISLV | FLVPVRLNQT | VIWDRPQVTF | 991 |
| CD11C | ESEEKES-HV | AMHRYQVNNL | GQRDLPVSIN | FWVPVELNQE | AVWMDVEVSH | 990 |
|       |            |            |            |            |            |     |
| αD    | SQSLP--CVS | ERKPPQHSDF | LTQISRSPML | DCSIADCLQF | RCDVPSFSVQ | 1035 |
| CD11B | SENLSSTCHT | KERLPSHSDF | LAELRKAPVV | NCSIAVCQRI | QCDIPFFGIQ | 1041 |
| CD11C | PQNPSLRCSS | EKIAPPASDF | LAHIQKNPVL | DCSIAGCLRF | RCDVPSFSVQ | 1040 |
|       |            |            |            |            |            |     |
| αD    | EELDFTLKGN | LSFGWVRETL | QKKVLVVSVA | EITFDTSVYS | QLPGQEAFMR | 1085 |
| CD11B | EEFNATLKGN | LSFDWYIKTS | HNHLLIVSTA | EILFNDSVFT | LLPGQGAFVR | 1091 |
| CD11C | EELDFTLKGN | LSFGWVRQIL | QKKVSVSVA  | EIIFDTSVYS | QLPGQEAFMR | 1090 |
|       |            |            |            |            |            |     |
| αD    | AQMEMVLEED | EVYNAIPIIM | GSSVGALLLL | ALITATLYKL | GFFKRHYKEM | 1135 |
| CD11B | SQTETKVEPF | EVPNPLPLIV | GSSVGGLLLL | ALITAALYKL | GFFKRQYKDM | 1141 |
| CD11C | AQTITVLEKY | KVHNPIPLIV | GSSIGGLLLL | ALITAVLYKV | GFFKRQYKEM | 1140 |
|       |            |            |            |            |            |     |
| αD    | LEDKPED--- | -----TATFS | GDDFSCVAPN | VPLS       |            | 1161 |
| CD11B | M---SEG--- | -----GP--P | GAE-----PQ | ----       |            | 1153 |
| CD11C | M---EEANGQ | IAPENGT--Q | TPS-----PP | SEK        |            | 1163 |

FIGURE 1D

HUMAN $\beta_2$ INTEGRIN $\alpha$ SUBUNIT

FIELD OF THE INVENTION

The present invention relates to the cloning and expression of nucleotide sequences encoding a novel human $\beta_2$ integrin $\alpha$ subunit, designated $\alpha_d$, which is structurally related to the known human $\beta_2$ integrin $\alpha$ subunits, CD11a, CD11b and CD11c.

BACKGROUND OF THE INVENTION

The integrins are a class of membrane-associated molecules which actively participate in cellular adhesion. Integrins are transmembrane heterodimers comprising an $\alpha$ subunit in noncovalent association with $\beta$ subunit. To date, at least fourteen $\alpha$ subunits and eight $\beta$ subunits have been identified [reviewed in Springer, Nature 346:425–434 (1990)]. The/ 62 subunits are generally capable of association with more than one $\alpha$ subunit and the heterodimers sharing a common $\beta$ subunit have been classified as subfamilies within the integrin population.

One class of human integrins, restricted to expression in white blood cells, is characterized by a common $\beta_2$ subunit. As a result of this cell-specific expression, these integrins are commonly referred to as the leukocyte integrins, Leu-CAMs or leukointegrins. Because of the common $\beta_2$ subunit, an alternative designation of this class is the $\beta_2$ integrins. The $\beta_2$ subunit (CD 18) has previously been isolated in association with one of three distinct $\alpha$ subunits, CD11a, CD11b or CD11c. The isolation of a cDNA encoding human CD18 is descibed in Kishimoto, et al., Cell 48:681-690 (1987). In official WHO nomenclature, the heterodimeric proteins are referred to as CD11a/CD18, CD11b/CD18, and CD11c/CD18; in common nomenclature they are referred to as LFA-1, Mac-1 or Mol and p150,95 or LeuM5, respectively [Cobbold, et al., in Leukocyte Typing III, McMichael (ed), Oxford Press, p.788 (1987)]. The human $\beta_2$ integrin $\alpha$ subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., J. Cell Biol. 108:703-712 (1989); CD11b, Corbi, et al., J. Biol. Chem. 263:12403-12411 (1988) and CD11c, Corbi, et al. EMBO J. 6:4023–4028 (1987)]. Putative homologs of the human $\beta_2$ integrin $\alpha$ and $\beta$ chains, defined by approximate similarity in molecular weight, have been variously identified in other species including monkeys and other primates [Letvin, et al., Blood 61:408–410 (1983)], mice [Sanchez-Madrid, et al., J.Exp. Med. 154:1517 (1981)], and dogs [Moore, et al., Tissue Antigens 36:211-220 (1990)].

The absolute molecular weights of presumed homologs from other species have been shown to vary significantly [see, e.g., Danilenko et al., Tissue Antigens 40:13-21 (1992)], and in the absence of sequence information, a definitive correlation between human integrin subunits and those identified in other species has not been possible. Moreover, variation in the number of members in a protein family has been observed between different species. Consider, for example, that more IgA isotypes have been isolated in rabbits than in humans [Burnett, et al., EMBO J. 8:4041–4047 (1989) and Schneiderman, et al., Proc. Natl. Acad. Sci.(USA) 86:7561-7565 (1989)]. Similarly, in humans, at least six variants of the metallothionine protein have been previously identified [Karin and Richards, Nature 299:797-802 (1982) and Varshney, et al., Mol. Cell. Biol. 6:26–37, (1986)], whereas in the mouse, only two such variants are in evidence [Searle, et al., Mol. Cell. Biol. 4:1221-1230 (1984)]. Therefore, existence of multiple members of a protein family in one species does not necessarily imply that corresponding family members exist in another species.

In the specific context of $\beta_2$ integrins, in dogs it has been observed that the presumed canine $\beta_2$ counterpart to the human CD 18 is capable of dimer formation with as many as four potentially distinct $\alpha$ subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth $\alpha$-like canine subunit also capable of association with the $\beta_2$ subunit, but having a unique molecular weight and restricted in expression to a subset of differentiated tissue macrophages.

Antibodies generated by immunization of hamsters with murine dendritic cells resulted in two anti-integrin antibodies [Metlay, et al., J. Exp. Med. 171:1753-1771 (1990)]. One antibody, 2E6, immunoprecipitated a predominant heterodimer with subunits having approximate molecular weights of 180 kD and 90 kD in addition to minor bands in the molecular weight range of 150-160 kD. The second antibody, N418, precipitated another apparent heterodimer with subunits having approximate molecular weights of 150 kD and 90 kD. Based on cellular adhesion blocking studies, it was hypothesized that antibody 2E6 recognized a murine counterpart to human CD18. While the molecular weight of the N418 antigen suggested recognition of a murine homolog to human CD11c/CD 18, further analysis indicated that the murine antigen exhibited a tissue distribution pattern which was inconsistent with that observed for human CD 11c/CD 18.

The antigens recognized by the canine Ca11.8H2 antibody and the murine N418 antibody could represent a variant species (e.g., a glycosylation or splice variant) of a previously identified canine or murine $\alpha$ subunit. Alternatively, these antigens may represent Unique canine and murine integrin $\alpha$ subunits. In the absence of specific information regarding primary structure, these alternatives cannot be distinguished.

In humans, CD11aJCD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11aJCD18 predominates on lymphocytes, CD11b/CD 18 on granulocytes and CD11c/CD 18 on macrophages [see review, Arnaout, Blood 75:1037-1050 (1990)]. Expression of the $\alpha$ chains, however, is variable with regard to the state of activation and differentiation of the individual cell types [See review, Larson and Springer, Immunol. Rev. 114:181-217 (1990).]

The involvement of the $\beta_2$ integrins in human immune and inflammatory responses has been demonstrated using monoclonal antibodies which are capable of blocking $\beta_2$ integrin-associated cell adhesion. For example, CD11a/CD18, CD11b/CD18 and CD11c/CD18 actively participate in natural killer (NK) cell binding to lymphoma and adenocarcinoma cells [Patarroyo, et al., *Immunol. Rev.* 114: 67-108 (1990) ], granulocyte accumulation [Nourshargh, et al., *J. Immunol.* 142:3193-3198 (1989)], granulocyte-independent plasma leakage [Arfors, et al., *Blood* 69:338-340 (1987)], chemotactic response of stimulated leukocytes [Arfors, et al., supra] and leukocyte adhesion to vascular endothelium [Price, et al., *J. Immunol.* 139:4174-4 177 (1987) and Smith, et al., *J. Clin. Invest.* 83:2008-2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. .LAD results from heterogeneous mutations in the $\beta_2$ subunit [Kishimoto, et al., *Cell* 50:193-202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra].

Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075-1078 (1989)]. This observation is consistent with the discovery that a principal counterreceptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and anti-sense strands) encoding a novel human $\beta_2$ integrin $\alpha_d$ subunit, $\alpha$ and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or the medium in which the host cell is grown. Host cells which express $\alpha_d$ polypeptides on the extracellular membrane surface are also useful as immunogens in the production of $\alpha_d$-specific antibodies. Preferably, host cells transfected with $\alpha_d$ will be co-transfected to express the $\beta_2$ subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ and $\alpha_d$ variant products of the invention may be obtained as isolates from natural sources, but are preferably produced by recombinant procedures involving host cells of the invention. Completely glycosylated, partially glycosylated and wholly de-glycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo.

The value of the information contributed through the disclosure of the DNA and amino acid sequences of $\alpha_d$ is manifest. In one series of examples, the disclosed $\alpha_d$ cDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ cDNA sequence as a probe to screen an appropriate library. Alternatively, polymerase chain reaction (PCR) using oligonucleotide primers that are designed based on the known cDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, Science 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transruction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\alpha_d$ mRNA and polypeptide products of the $\alpha_d$ gene.

Identification of cell types which express $\alpha_d$ may have significant ramifications for development of therapeutic and prophylactic agents. For example, if $\alpha_d$ is the homolog of the canine protein recognized by the antibody Ca11.8H2, the expression of which is restricted to tissue macrophages, recombinant human $\alpha_d$ may allow for design of drugs potentially useful to combat disease states such as atherosclerosis, multiple sclerosis and type I diabetes commonly associated with this cell type.

BRIEF DESCRIPTION OF THE DRAWING

Numerous other aspects and advantages of the present invention will be apparent upon consideration of the following description thereof, reference being made to the drawing wherein:

FIG. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$ antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissue and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD 18 in association with $\alpha_d$ in co-transfected COS cells. Example 11 relates to production of $\alpha_d$-specific monoclonal antibodies.

EXAMPLE 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically $1 \times 10^6$ cells) were incubated with undiluted hybridoma supernatant or a purified mouse IgG-negative control antibody (10 µg/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 µg/ml. Stained cells were fixed with 2 % w/v paraformaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$.

Because the toonotional antibody Ca11.8H2 specific for the canine $\alpha$ subunit did not cross react with a human homolog, isolation of canine $\alpha_{TM1}$ DNA was deemed a necessary prerequisite to isolate a counterpart human gene if one existed.

EXAMPLE 2

Affinity Purification Of Canine $\alpha_{TM1}$ For N-Terminal Sequencing

Canine $\alpha_{TM1}$ was affinity purified in order to determine N-terminal amino acid sequences for oligonucleotide probe/primer design. Briefly, anti-$\alpha_{TM1}$ monoclonal antibody Ca11.8H2 was coupled to Affigel 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1M ethanolamine. The resin was then washed with thirty column volumes of phosphate buffered saline (PBS).

Twenty-five grams of a single dog spleen were homogenized in 250 ml of buffer containing 0.32M sucrose in 25 mM Tris-HCl, pH 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2 % NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Ca11.8H2-conjugated Affigel 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1M Tris-HCl, pH 6.8, 2% SDS, 20% glycerol and 0.002% bromophenol blue. The resin was pelleted by centrifugation and discarded; the supernatant was treated with 1/15 volume β-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore-filtered water and equilibrated for 15–45 minutes in 10 mM 3-[cyclohexylamino]-1-propanesulfonic acid (CAPS) transfer buffer, pH 10.5, with 10% methanol. hnmobilon membranes were moistened with methanol, rinsed with filtered water, and equilibrated for 15–30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were de-stained in 50% methanol/10% acetic acid three times, ten minutes each time. After desmining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

FNLDVEEPMVFQ (SEQ ID NO: 5)

The identified sequence included the FNLD sequence characteristic of α subunits of the integrin family [Tamura, et al., J. Cell. Biol. 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patruer," a partially degenerate oligonucleotide; and c) "Guessruer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

5'-TTYAAYYTGGAYGTNGARGARC-CNATGGTNTTYCA-3' (SEQ ID NO: 6)

5'-TTCAACCTGGACGTGGAGGAGC-CCATGGTGTTCCAA-3' (SEQ ID NO: 7)

5'-TTCAACCTGGACGTNGAASANC-CCATGGTCTTCCAA-3' (SEQ ID NO: 8)

Based on sequencing data, no relevant clones were detected using these oligonucleotides in several low stringency hybridizations to a canine spleen/peripheral blood macrophage cDNA library cloned into λZAP (Stratagene, La Jolla, Calif.).

Four other oligonucleotide primers, designated 5'Deg, 5'Spec, 3'Deg and 3'Spec (asset out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

5'-TTYAAYYTNGAYGTNGARGARCC-3' (SEQ ID NO: 9)

5'-TTYAAYYTGGACGTNGAAGA-3' (SEQ ID NO: 10)

5'-TGRAANACCATNGGYTC-3' (SEQ ID NO: 11)

5'-TTGGAAGACCATNGGYTC-3' (SEQ ID NO: 12)

The $\alpha_{TM1}$ oligonucleotide primers were paired with T3 or T7 vector sequence primers, as set out in SEQ ID NOS: 13 and 14, respectively, which hybridize to sequences flanking the polylinker region in the Bluescript phagemid found in λZAP.

5'-ATTAACCCTCACTAAAG-3' (SEQ ID NO: 13)

5'-AATACGACTCACTATAG-3' (SEQ ID NO: 14)

The PCR amplification was carried out in Taq buffer (Boehringer Mannheim, Indianapolis, Ind.) containing magnesium with 150 ng of library DNA, 1 μg of each primer, 200 μM dNTPs and 2.5 units Taq polymerase (Boehringer Mannheim) and the products were separated by electrophoresis on a 1% agarose gel in Tris-Acetate-EDTA (TAE) buffer with 0.25 μg/ml ethidium bromide. DNA was transferred to a Hybond (Amersham, Arlington, Heights, Ill.) membrane by wicking overnight in 10X SSPE. After transfer, the immobilized DNA was denatured with 0.5M NaOH with 0.6M NaCl, neutralized with 1.0M Tris-HCl, pH 8.0, in 1.5M NaCl, and washed with 2X SSPE before UV cross-linking with a Stratalinker (Stratagene) cross-linking apparatus. The membrane was incubated in prehybridization buffer (5X SSPE, 4X Denhardts, 0.8% SDS, 30% formamide) for 2 hr at 50° C. with agitation.

Oligonucleotide probes 5 'Deg, 5 'Spec, 3 'Deg and 3'Spec (SEQ ID NOS: 9, 10, 11 and 12, respectively) were labeled using a Boehringer Mannheim kinase buffer with 100–300 $\mu$Ci $\gamma P^{32}$-dATP and 1–3 units of polynucleotide kinase for 1–3 hr at 37° C. Unincorporated label was removed with Sephadex G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1X SSPE/0.1% SDS at 50° for 15 min. The blot was then exposed to Kodak X-Omat AR film for 1–4 hours at −80° C.

The oligonucleotides 5'Deg, 5'Spec, 3'Deg and 3'Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

EXAMPLE 3

Large Scale Affinity Purification Of Canine $\alpha_{TM1}$ For Internal Sequencing In order to provide additional amino acid sequence for primer design, canine $\alpha_{TM1}$ was purified for internal sequencing. Three sections of frozen spleen (approximately 50 g each) and frozen cells from two partial spleens from adult dogs were used to generate protein for internal sequencing. Fifty grams of spleen were homogenized in 200–300 ml borate buffer with a Waring blender. The homogenized material was diluted with 1 volume of buffer containing 4 % NP-40, and the mixture then gently agitated for at least one hour. The resulting lysate was cleared of large debris by centrifugation at 2000 g for 20 rain, and then filtered through either a Corning (Coming, N.Y.) prefilter or a Corning 0.8 micron filter. The lysate was further clarified by filtration through the Corning 0.4 micron filter system.

Splenic lysate and the antibody-conjugated Affigel 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel 10 resin and incubated overnight as above. The absorbed resin aliquots were then combined and washed with 50 volumes D-PBS/0.19 Tween 20 and the resin transferred to a 50 ml Biorad column. Adsorbed protein was eluted from the resin with 3–5 volumes of 0.1M glycine (pH 2.5); fractions of approximately 900 $\mu$l were collected and neutralized with 100 $\mu$l 1M Tris buffer, pH 8.0. Aliquots of 15 $\mu$l were removed from each fraction and boiled in an equal volume of 2X Laemmli sample buffer with 1/15 volume 1M dithiothreitol (DTT). These samples were electrophoresed on 8 9 Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 509 with reducing Laemmli sample buffer and run on 1.5 mm 79 polyacrylamide gels in Tris-glycine/SDS buffer. Protein was transferred from the gels to Immobilon membrane by the procedure described in Example 2 using the Hoefer transfer apparatus.

The protein bands corresponding to canine $\alpha_{d1}$ were excised from 10 PVDF membranes and resulted in approximately 47 $\mu$g total protein. The bands were destained in 4 ml 50% methanol for 5 minutes, air dried and cut into 1×2 mm pieces. The membrane pieces were submerged in 2 ml 95 9 acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 709 formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 $\mu$l 8M urea, 0.4M $NH_4HCO_3$. The fragments were reduced in 5 $\mu$l 45 mM dithiothreitol (DTT) and subsequently incubated at 50° C. for 15 minutes. The solution was then cooled to room temperature and the fragments alkylated by adding 5 $\mu$l 100 mM iodoacetamide (Sigma, St. Louis, Mo.). Following a 15 minute incubation at room temperature, the sample was diluted with 187 $\mu$l Milli Q water to a final urea concentration of 2.0M. Trypsin (Worthington, Freehold, N.J.) was then added at a ratio of 1:25 (w:w) of enzyme to protein and the protein digested for 24 hours at 37° C. Digestion was terminated with addition of 30 $\mu$l TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05 % TFA and HPLC water (buffer A). The peptides were eluted with increasing concentration of 80% acetonitrile in 0.04 % TFA (buffer B) with a gradient of 38–75 % buffer B for 65–95 minutes and 75–98 % buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program, Version 1.2.1. All sequencing reagents were supplied by Applied Biosystems. The amino acid sequences of seven of the eight internal fragments are set out below wherein "X" indicates the identity of the amino acid was not certain.

VFQEXGAGFGQ (SEQ ID NO: 15)

LYDXVAATGLXQPI (SEQ ID NO: 16)

PLEYXDVIPQAE (SEQ ID NO: 17)

FQEGFSXVLX (SEQ ID NO: 18)

TSPTFIXMSQENVD (SEQ ID NO: 19)

LVVGAPLEVVAVXQTGR (SEQ ID NO: 20)

LDXKPXDTA (SEQ ID NO: 21)

Primer Design

One internal amino acid sequence (set out in SEQ ID NO: 22) obtained was then used to design a fully degenerate oligonucleotide primer, designated p4(R) as set out in SEQ ID NO: 23.

FGEQFSE (SEQ ID NO: 22) 5
'-RAANCCYTCYTGRAAACTYTC-3' (SEQ ID NO: 23)

EXAMPLE 4

PCR Cloning Of A Canine $\alpha_{TM1}$ Fragment

The 5' portion of the canine $\alpha_{TM1}$ gene was amplified from double-stranded canine splenic cDNA by PCR.

A. Generation of Double Stranded Canine Spleen cDNA

One gram of frozen material from a juvenile dog spleen was ground in liquid nitrogen on dry ice and homogenized in 20 ml RNA-Stat 60 buffer (Tel-Test B, Inc, Friendswood, Tex.). Four ml chloroform were added, and the solution extracted by centrifugation at 12,000 g for 15 minutes. RNA was precipitated from the aqueous layer with 10 ml ethanol. Poly A+RNA was then selected on Dynal Oligo dT Dynabeads (Dynal, Oslo, Norway). Five aliquots of 100 μg total RNA were combined and diluted with an equal volume of 2X binding buffer (20 mM Tris-HCl, pH 7.5, 1.0M LiCl, 1 mM EDTA, 0.1% SDS). RNA was then incubated 5 minutes with the Oligo dT Dynabeads (1.0 ml or 5 mg beads for all the samples). Beads were washed with buffer containing 10 mM Tris-HCl, pH 7.5, 0.15M LiCl, 1 mM EDTA and 0.1% SDS, according to the manufacturer's suggested protocol prior to elution of poly A+mRNA with 2 mM EDTA, pH 7.5. Double-stranded eDNA was then generated using the eluted poly A+ mRNA and the Boehfinger Mannhelm eDNA Synthesis Kit according to the manufacturer's suggested protocol.

B. Isolation of a Partial Canine $\alpha_{TM1}$ CDNA

Oligonucleotide primers 5 'Deg (SEQ ID NO: 9) and p4(R) (SEQ ID NO: 23) were employed in a standard PCR reaction using 150 ng double-stranded cDNA, 500 ng of each primer, 200 μM dNTPs and 1.5 units Taq polymerase (Boehringer Mannheim) in Taq buffer (Boehringer Mannheim) with magnesium. The resulting products (1 μl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, pH 8, 1 mM EDTA, 1.5M NaCl at 65° C., precipitated, and ligated into the pCR$^{tm}$II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha_{TM1}$ peptide sequences which were not utilized in design of the primers. The sequence of the entire insert of clone 2.7 is set out in SEQ ID NO: 24.

Attempts to isolate the full length canine $\alpha_{TM1}$ CDNA from the Stratagene library (as described in Example 2) were unsuccessful. Approximately $1 \times 10^6$ phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved α subunit amino acid motif GFFKR [Tamura, et al., supra] were also unsuccessful.

EXAMPLE 5

Cloning Of A Putative Human Homolog Of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 23) primers.

5'-GTNTTYCARGARGAYGG-3' (SEQ ID NO: 25)

The PCR product was purified using the Qiagen (Chatsworth, Ga.) Quick Spin kit and the manufacturer's suggested protocol. The purified DNA (200 ng) was labeled with 200 μCi $\alpha^{32}$PdCTP using the Boehringer Mannheim Random Prime Labelling kit and the manufacturer's suggested protocol. Unincorporated isotope was removed with Sephadex G25 (fine) gravity chromatography. The probe was denatured with 0.2N NaOH and neutralized with 0.4M Tris-HCl, pH 8.0, before use.

Colony lifts on Hybond filters (Amersham) of a human spleen cDNA library in pCDNA/Amp (Invitrogen) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2X SSC/0.1% SDS at 37° C. and twice in 2X SSC/0.1% SDS at 50° C. Final stringency washes were 1X SSC/0.1% SDS, twice at 65° C. (1X SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1 X SSC/0.1% SDS at 65'C and exposed to Kodak X-Omat AR film for 2.5 hours at −80° C. with an intensifying screen. Positive colonies were identified and cultured in LBM/carbenicillin medium overnight. DNA from the cultures was prepared using the Promega Wizard miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics Of The Human $\alpha_d$ CDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11 c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the I (insertion) domain common to CD11a, CD11b and CD11c [Larson and Springer, supra] and in VLA-2 [Tamura, et al., supra]. This region has not been demonstrated to exist in any other integrin subunits.

The deduced amino acid sequence of $\alpha_d$ shows approximately 28 % identity to that of CD11a, approximately 58% identity to CD11b and approximately 61% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

EXAMPLE 6

Northern Analysis of Human $\alpha_d$ Expression in Tissues

In order to determine the relative level of expression and tissue specificity of $\alpha_d$, Northern analysis was performed using a fragment from clone 19A2 as a probe. Approximately 10 μg of total RNA from each of several human tissues were loaded on a formaldehyde agarose gel in the presence of 1 μg of ethidium bromide. After electrophoresis at 100 V for 4 hr, the RNA was transferred to a nitrocellulose membrane (Schleicher & Schuell) by wicking in 10X SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. A 1.6 kb BstXI fragment of clone 19A2 was labeled with the Boehringer Mannheim Random Prime kit according to the manufacturer's instructions including both $\alpha P^{32}dCTP$ and $\alpha P^{32}dTTP$. Unincorporated label was removed on a Sephadex G25 column in TE buffer. The membrane was probed with $1.5 \times 10^6$ counts per ml of prehybridization buffer. The blot was then washed successively with 2X SSC/0.1% SDS at room temperature, 2X SSC/0.1% SDS at 42° C., 2X SSC/0.1% SDS at 50OC, 1X SSC/0.1% SDS at 50° C., 0.5X SSC/0.1% SDS at 50° C. and 0.1X SSC/0.1% SDS at 50° C. The blot was then exposed to film for 19 hr.

The autoradiogram revealed a weak signal in the approximately 5 kb range in liver, placenta, thymus and tonsil total RNA. No signal was detected in kidney, brain or heart samples. The amount of RNA present in the kidney lane, however, was minimal. RNA from three myeloid lineage cell lines was also probed. The THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however, PMA treatment seemed to increase the signal intensity. U937 cells expressed the $\alpha_d$ message and this signal did not increase with PMA stimulation.

EXAMPLE 7

Expression Of Human $\alpha_d$ Constructs

A. Generation of expression constructs

The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added on at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical nonspecific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer ER1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is underlined and the EcoRI site is double underlined.

Primer BamRev 5
 '-CCACTGTCAGGATGCCCGTG-3' (SEQ ID NO: 26)

Primer ER1B 5
 '-AGTTACGAATTCGCCACCATGGCT-

CTACGGGTGCTTCTTCTG-3' (SEQ ID NO: 27)

Primer ER1C 5
'-AGTTACGAATTCGCCACCATGACTC-
GGACTGTGCTTCTTCTG-3' (SEQ ID NO: 28)

Primer ER1D 5
'-AGTTACGAATTCGCCACCAT-
GACCTTCGGCACTGTG-3' (SEQ ID NO: 29)

The resulting PCR product was digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal sequences. The clones were designated pATM.B1 (CD11b/$\alpha_d$, from primer ER1B), pATM.C10 (CD11c/$\alpha_d$, from primer ER1C) and pATM.D12 (adenosine/$\alpha_d$ from primer ER1 d). Presence of the appropriate signal sequences in each clone were verified by nucleic acid sequencing.

B. Transfection of COS Cells

Expression from the $\alpha_d$ plasmids discussed above was effected by cotransfection of COS cells with the individual plasmids and a CD 18 expression plasmid, pRC.CD18. As a positive control, COS cells were also co-transfected with the plasmid pRC.CD18 and a CD11a expression plasmid, pDC.CD11A.

Cells were passaged in culture medium (DMEM/10%FBS/pen-strep) into 10 cm Corning tissue culture-treated petri dishes at 50 % confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 μg/ml DEAE-Dextran and 0.5 mM chloroquine) on each plate. After 1.5 hours incubation at 37° C., the cells were shocked for 1 minute with 5 ml DMEM/10% DMSO. This DMSO solution was then replaced with 10 ml/plate culture medium.

Resulting transfectants were analyzed by ELISA and FACS as described below.

EXAMPLE 8

ELISA Analysis of COS Transfectants

In order to determine if the COS cells co-transfected with CD 18 expression plasmid pRC. CD 18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a CD11a expression plasmid, pDC.CD11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150 μl/well D-PBS/0.5 % teleost skin gelatin (Sigma) solution. This buffer was used in all steps except during the development. All washes and incubations were performed at room temperature. The wells were blocked with gelatin solution for 1 hour. Primary antibodies were diluted to 10 μg/ml in gelatin solution and 50 μl were then added to each well. Triplicate wells were set up for each primary antibody. After 1 hour incubation, plates were washed 3X with 150 μl/well gelatin solution. Secondary antibody (goat anti-mouse Ig/HRP-Fc specific [Jackson, West Grove, Pa.]) at a 1:3500 dilution was added at 50 μl/well and plates were incubated for 1 hour. After three washes, plates were developed with 100 μl/well O-phenyldiamine (OPD) (Sigma) solution (1 mg/ml OPD in citrate buffer) and the plates were allowed to develop for 20 minutes before addition of 50 μl/well 15 % sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the $\alpha_d$ expression constructs (pATM.C10 or pATM.D12) revealed that cell surface expression of CD18 was rescued by concomitant expression of $\alpha_d$. The increase in detectable CD18 expression in COS cells transfected with pATM.C10 or pATM.D12 was comparable to that observed in co-transfected CD 11a/CD 18 positive control cells.

EXAMPLE 9

FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, CD11b specific antibodies (Becton Dickinson) or 800 μg/ml CFSE-conjugated murine 23F2G (anti-CD18) (ATCC HB11081 ) were added to each sample. Samples were then incubated on ice for 45 minutes, washed 3× with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD 11a or CD 18. All cells transfected with CD18 and any $\alpha_d$ construct resulted in no detectable staining for CD11a and CD11b. The pATM.B1, pATM.C10 and pATM.D12 groups stained 4%, 13% and 8 % positive for CD 18, respectively. Fluorescence of the positive population in the CD11a/CD18 group was 4-fold higher than background. In comparison, the co-transfection of $\alpha_d$ constructs with the CD18 construct produced a positive population that showed a 4- to 7-fold increase in fluorescence intensity over background.

EXAMPLE 10

Biotin-Labeled Immunoprecipitation of CD18/$\alpha_d$ Complexes from Co-transfected COS Cells Immunoprecipitation was attempted on cells co-transfected with CD 18 and each of the $\alpha_d$ expression plasmids separately described in Example 7 in order to determine if $\alpha_d$ could be isolated as part of the $\alpha\beta$ heterodimer complex characteristic of integrins.

Transfected cells ($1-3 \times 10^8$ cells/group) were removed from petri dishes with Vetserie buffer and washed 3 times in 50 ml/group D-PBS. Each sample was labeled with 2 mg Sulpho-NHS Biotin (Pierce, Rockford, Ill. for 15 minutes at room temperature. The reaction was quenched by washing 3 times in 50 ml/sample cold D-PBS. Washed cells were resuspended in 1 ml lysis buffer (1% NP40, 50 mM Tris-HCl, pH 8.0, 0.2M NaCl, 2 mM Ca++, 2 mM Mg++, and protease inhibitors) and incubated 15 minutes on ice. Insoluble material was pelleted by centrifugation at 10,000 g for 5 minutes, and the supernatant removed to fresh tubes. In order to remove material non-specifically reactive with mouse immunoglobulin, a pre-clearance step was initially performed. Twenty-five micrograms mouse immunoglobulin (Cappel, West Chester, Pa.) was incubated with supernatants at 4° C. After 2.5 hr, 100 μl (25 μg) rabbit anti-mouse Ig conjugated sepharose (prepared from Protein A Sepharose 4B and rabbit anti-mouse IgG, both from Zymed, San Francisco, Calif.) was added to each sample; incubation was continued at 4° C. with rocking for 16 hours. Sepharose beads were removed from the supernatants by centrifugation. After pre-clearance, the supernatants were then treated with 20 μg anti-CD18 antibody (TS1.18) for 2 hours at 4° C. Antibody/antigen complexes were isolated from supernatants by incubation with 100 μl/sample rabbit anti-mouse/Protein A-sepharose preparation described above. Beads were washed 4 times with 10 mM HEPES, 0.2M NaCl, and 1% Triton-X 100. Washed beads were pelleted and boiled for 10 minutes in 20 μl 2X Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3 % BSA in TBS-T. Membranes were treated with 1:6000 dilution of Strep-avidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an α chain of approximately 150 kD, corresponding to $\alpha_d$.

EXAMPLE 11

Production of $\alpha_d$ Monoclonal Antibodies

Transiently transfected cells from Example 7 were washed three times in Dulbecco's phosphate buffered saline (D-PBS) and injected at $5 \times 10^6$ cells/mouse into Balb/c mice with 50 μg/mouse muramyl dipeptidase (Sigma) in PBS. Mice are injected two more times in the same fashion at two week intervals. The pre-bleed and immunized serum from the mice is screened by FACS analysis as outlined in Example 9 and the spleen from the mouse with the highest reactivity to cells transfected with $\alpha_d$/CD 18 is fused. Hybridoma culture supernatants are then screened separately for lack of reactivity against COS cells transfected with CD11a/CD18 and for reactivity with cells co-transfected with an $\alpha_d$ expression plasmid and CD18.

Numerous modifications and variations in the invention as set forth in the above illustrative examples are expected to occur to those skilled in the art. Consequently only such limitations as appear in the appended claims should be placed on the invention.

---

What is claimed is:

1. A purified and isolated $\alpha_d$ polynucleotide consisting of the human $\alpha_d$ protein coding sequence set out in SEQ ID NO: 1.

2. The polynucleotide of claim 1 which is a DNA molecule.

3. The DNA molecule of claim 2 which is a cDNA molecule.

4. The DNA molecule of claim 2 which is a genomic DNA molecule.

5. The DNA molecule of claim 2 which is a wholly or partially chemically synthesized DNA molecule.

6. A full length purified and isolated $\alpha_d$ encoding polynucleotide selected from the group consisting of:
    a) the human DNA sequence set out in SEQ ID NO: 1, and
    b) a DNA molecule which hybridizes under stringent conditions to the protein coding portion of the DNA of a).

7. A DNA molecule encoding the human $\alpha_d$ amino acid sequence set out in SEQ ID NO: 2.

8. A DNA expression construct comprising a DNA molecule according to claim 2.

9. A host cell transformed with a DNA molecule according to claim 2.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
      ( A ) LENGTH: 3726 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:

(A) NAME/KEY: CDS
(B) LOCATION: 3..3485

(xi) SEQUENCE DESCRIPTION: SEQ ID NO:1:

```
TG ACC TTC GGC ACT GTG CTT CTT CTG AGT GTC CTG GCT TCT TAT CAT        47
   Thr Phe Gly Thr Val Leu Leu Leu Ser Val Leu Ala Ser Tyr His
   1             5                   10                  15

GGA TTC AAC CTG GAT GTG GAG GAG CCT ACG ATC TTC CAG GAG GAT GCA       95
Gly Phe Asn Leu Asp Val Glu Glu Pro Thr Ile Phe Gln Glu Asp Ala
                20                  25                  30

GGC GGC TTT GGG CAG AGC GTG GTG CAG TTC GGT GGA TCT CGA CTC GTG      143
Gly Gly Phe Gly Gln Ser Val Val Gln Phe Gly Gly Ser Arg Leu Val
            35                  40                  45

GTG GGA GCA CCC CTG GAG GTG GTG GCG GCC AAC CAG ACG GGA CGG CTG      191
Val Gly Ala Pro Leu Glu Val Val Ala Ala Asn Gln Thr Gly Arg Leu
        50                  55                  60

TAT GAC TGC GCA GCT GCC ACC GGC ATG TGC CAG CCC ATC CCG CTG CAC      239
Tyr Asp Cys Ala Ala Ala Thr Gly Met Cys Gln Pro Ile Pro Leu His
    65                  70                  75

ATC CGC CCT GAG GCC GTG AAC ATG TCC TTG GGC CTG ACC CTG GCA GCC      287
Ile Arg Pro Glu Ala Val Asn Met Ser Leu Gly Leu Thr Leu Ala Ala
80                  85                  90                  95

TCC ACC AAC GGC TCC CGG CTC CTG GCC TGT GGC CCG ACC CTG CAC AGA      335
Ser Thr Asn Gly Ser Arg Leu Leu Ala Cys Gly Pro Thr Leu His Arg
                100                 105                 110

GTC TGT GGG GAG AAC TCA TAC TCA AAG GGT TCC TGC CTC CTG CTG GGC      383
Val Cys Gly Glu Asn Ser Tyr Ser Lys Gly Ser Cys Leu Leu Leu Gly
            115                 120                 125

TCG CGC TGG GAG ATC ATC CAG ACA GTC CCC GAC GCC ACG CCA GAG TGT      431
Ser Arg Trp Glu Ile Ile Gln Thr Val Pro Asp Ala Thr Pro Glu Cys
        130                 135                 140

CCA CAT CAA GAG ATG GAC ATC GTC TTC CTG ATT GAC GGC TCT GGA AGC      479
Pro His Gln Glu Met Asp Ile Val Phe Leu Ile Asp Gly Ser Gly Ser
    145                 150                 155

ATT GAC CAA AAT GAC TTT AAC CAG ATG AAG GGC TTT GTC CAA GCT GTC      527
Ile Asp Gln Asn Asp Phe Asn Gln Met Lys Gly Phe Val Gln Ala Val
160                 165                 170                 175

ATG GGC CAG TTT GAG GGC ACT GAC ACC CTG TTT GCA CTG ATG CAG TAC      575
Met Gly Gln Phe Glu Gly Thr Asp Thr Leu Phe Ala Leu Met Gln Tyr
                180                 185                 190

TCA AAC CTC CTG AAG ATC CAC TTC ACC TTC ACC CAA TTC CGG ACC AGC      623
Ser Asn Leu Leu Lys Ile His Phe Thr Phe Thr Gln Phe Arg Thr Ser
            195                 200                 205

CCG AGC CAG CAG AGC CTG GTG GAT CCC ATC GTC CAA CTG AAA GGC CTG      671
Pro Ser Gln Gln Ser Leu Val Asp Pro Ile Val Gln Leu Lys Gly Leu
        210                 215                 220

ACG TTC ACG GCC ACG GGC ATC CTG ACA GTG GTG ACA CAG CTA TTT CAT      719
Thr Phe Thr Ala Thr Gly Ile Leu Thr Val Val Thr Gln Leu Phe His
    225                 230                 235

CAT AAG AAT GGG GCC CGA AAA AGT GCC AAG AAG ATC CTC ATT GTC ATC      767
His Lys Asn Gly Ala Arg Lys Ser Ala Lys Lys Ile Leu Ile Val Ile
240                 245                 250                 255

ACA GAT GGG CAG AAG TAC AAA GAC CCC CTG GAA TAC AGT GAT GTC ATC      815
Thr Asp Gly Gln Lys Tyr Lys Asp Pro Leu Glu Tyr Ser Asp Val Ile
                260                 265                 270

CCC CAG GCA GAG AAG GCT GGC ATC ATC CGC TAC GCT ATC GGG GTG GGA      863
Pro Gln Ala Glu Lys Ala Gly Ile Ile Arg Tyr Ala Ile Gly Val Gly
            275                 280                 285

CAC GCT TTC CAG GGA CCC ACT GCC AGG CAG GAG CTG AAT ACC ATC AGC      911
His Ala Phe Gln Gly Pro Thr Ala Arg Gln Glu Leu Asn Thr Ile Ser
        290                 295                 300

TCA GCG CCT CCG CAG GAC CAC GTG TTC AAG GTG GAC AAC TTT GCA GCC      959
```

-continued

| | | | | | | | | | | | | | | |
|---|---|---|---|---|---|---|---|---|---|---|---|---|---|---|
| Ser | Ala | Pro | Pro | Gln | Asp | His | Val | Phe | Lys | Val | Asp | Asn | Phe | Ala | Ala |
| | 305 | | | | 310 | | | | 315 | | | | | | |

| CTT | GGC | AGC | ATC | CAG | AAG | CAG | CTG | CAG | GAG | AAG | ATC | TAT | GCA | GTT | GAG | 1007 |
|---|---|---|---|---|---|---|---|---|---|---|---|---|---|---|---|---|
| Leu | Gly | Ser | Ile | Gln | Lys | Gln | Leu | Gln | Glu | Lys | Ile | Tyr | Ala | Val | Glu | |
| 320 | | | | 325 | | | | | 330 | | | | | | 335 | |

| GGA | ACC | CAG | TCC | AGG | GCA | AGC | AGC | TCC | TTC | CAG | CAC | GAG | ATG | TCC | CAA | 1055 |
| Gly | Thr | Gln | Ser | Arg | Ala | Ser | Ser | Ser | Phe | Gln | His | Glu | Met | Ser | Gln | |
| | | | | 340 | | | | | 345 | | | | | 350 | | |

| GAA | GGC | TTC | AGC | ACA | GCC | CTC | ACA | ATG | GAT | GGC | CTC | TTC | CTG | GGG | GCT | 1103 |
| Glu | Gly | Phe | Ser | Thr | Ala | Leu | Thr | Met | Asp | Gly | Leu | Phe | Leu | Gly | Ala | |
| | | | 355 | | | | | 360 | | | | | 365 | | | |

| GTG | GGG | AGC | TTT | AGC | TGG | TCT | GGA | GGT | GCC | TTC | CTG | TAT | CCC | CCA | AAT | 1151 |
| Val | Gly | Ser | Phe | Ser | Trp | Ser | Gly | Gly | Ala | Phe | Leu | Tyr | Pro | Pro | Asn | |
| | | 370 | | | | | 375 | | | | | 380 | | | | |

| ATG | AGC | CCC | ACC | TTC | ATC | AAC | ATG | TCT | CAG | GAG | AAT | GTG | GAC | ATG | AGG | 1199 |
| Met | Ser | Pro | Thr | Phe | Ile | Asn | Met | Ser | Gln | Glu | Asn | Val | Asp | Met | Arg | |
| | 385 | | | | | 390 | | | | | 395 | | | | | |

| GAC | TCT | TAC | CTG | GGT | TAC | TCC | ACC | GAG | CTA | GCC | CTG | TGG | AAG | GGG | GTA | 1247 |
| Asp | Ser | Tyr | Leu | Gly | Tyr | Ser | Thr | Glu | Leu | Ala | Leu | Trp | Lys | Gly | Val | |
| 400 | | | | | 405 | | | | | 410 | | | | | 415 | |

| CAG | AAC | CTG | GTC | CTG | GGG | GCC | CCC | CGC | TAC | CAG | CAT | ACC | GGG | AAG | GCT | 1295 |
| Gln | Asn | Leu | Val | Leu | Gly | Ala | Pro | Arg | Tyr | Gln | His | Thr | Gly | Lys | Ala | |
| | | | | 420 | | | | | 425 | | | | | 430 | | |

| GTC | ATC | TTC | ACC | CAG | GTG | TCC | AGG | CAA | TGG | AGG | AAG | AAG | GCC | GAA | GTC | 1343 |
| Val | Ile | Phe | Thr | Gln | Val | Ser | Arg | Gln | Trp | Arg | Lys | Lys | Ala | Glu | Val | |
| | | | 435 | | | | | 440 | | | | | 445 | | | |

| ACA | GGG | ACG | CAG | ATC | GGC | TCC | TAC | TTC | GGG | GCC | TCC | CTC | TGC | TCC | GTG | 1391 |
| Thr | Gly | Thr | Gln | Ile | Gly | Ser | Tyr | Phe | Gly | Ala | Ser | Leu | Cys | Ser | Val | |
| | | 450 | | | | | 455 | | | | | 460 | | | | |

| GAT | GTG | GAC | AGC | GAT | GGC | AGC | ACC | GAC | CTG | ATC | CTC | ATT | GGG | GCC | CCC | 1439 |
| Asp | Val | Asp | Ser | Asp | Gly | Ser | Thr | Asp | Leu | Ile | Leu | Ile | Gly | Ala | Pro | |
| | 465 | | | | | 470 | | | | | 475 | | | | | |

| CAT | TAC | TAT | GAG | CAG | ACC | CGA | GGG | GGC | CAG | GTG | TCC | GTG | TGT | CCC | TTG | 1487 |
| His | Tyr | Tyr | Glu | Gln | Thr | Arg | Gly | Gly | Gln | Val | Ser | Val | Cys | Pro | Leu | |
| 480 | | | | | 485 | | | | | 490 | | | | | 495 | |

| CCT | AGG | GGG | CAG | AGG | GTG | CAG | TGG | CAG | TGT | GAC | GCT | GTT | CTC | CGT | GGT | 1535 |
| Pro | Arg | Gly | Gln | Arg | Val | Gln | Trp | Gln | Cys | Asp | Ala | Val | Leu | Arg | Gly | |
| | | | | 500 | | | | | 505 | | | | | 510 | | |

| GAG | CAG | GGC | CAC | CCC | TGG | GGC | CGC | TTT | GGG | GCA | GCC | CTG | ACA | GTG | TTG | 1583 |
| Glu | Gln | Gly | His | Pro | Trp | Gly | Arg | Phe | Gly | Ala | Ala | Leu | Thr | Val | Leu | |
| | | | 515 | | | | | 520 | | | | | 525 | | | |

| GGG | GAT | GTG | AAT | GAG | GAC | AAG | CTG | ATA | GAC | GTG | GCC | ATT | GGG | GCC | CCG | 1631 |
| Gly | Asp | Val | Asn | Glu | Asp | Lys | Leu | Ile | Asp | Val | Ala | Ile | Gly | Ala | Pro | |
| | | 530 | | | | | 535 | | | | | 540 | | | | |

| GGA | GAG | CAG | GAG | AAC | CGG | GGT | GCT | GTC | TAC | CTG | TTT | CAC | GGA | GCC | TCA | 1679 |
| Gly | Glu | Gln | Glu | Asn | Arg | Gly | Ala | Val | Tyr | Leu | Phe | His | Gly | Ala | Ser | |
| | 545 | | | | | 550 | | | | | 555 | | | | | |

| GAA | TCC | GGC | ATC | AGC | CCC | TCC | CAC | AGC | CAG | CGG | ATT | GCC | AGC | TCC | CAG | 1727 |
| Glu | Ser | Gly | Ile | Ser | Pro | Ser | His | Ser | Gln | Arg | Ile | Ala | Ser | Ser | Gln | |
| 560 | | | | | 565 | | | | | 570 | | | | | 575 | |

| CTC | TCC | CCC | AGG | CTG | CAG | TAT | TTT | GGG | CAG | GCG | CTG | AGT | GGG | GGT | CAG | 1775 |
| Leu | Ser | Pro | Arg | Leu | Gln | Tyr | Phe | Gly | Gln | Ala | Leu | Ser | Gly | Gly | Gln | |
| | | | | 580 | | | | | 585 | | | | | 590 | | |

| GAC | CTC | ACC | CAG | GAT | GGA | CTG | ATG | GAC | CTG | GCC | GTG | GGG | GCC | CGG | GGC | 1823 |
| Asp | Leu | Thr | Gln | Asp | Gly | Leu | Met | Asp | Leu | Ala | Val | Gly | Ala | Arg | Gly | |
| | | | 595 | | | | | 600 | | | | | 605 | | | |

| CAG | GTG | CTC | CTG | CTC | AGG | AGT | CTG | CCG | GTG | CTG | AAA | GTG | GGG | GTG | GCC | 1871 |
| Gln | Val | Leu | Leu | Leu | Arg | Ser | Leu | Pro | Val | Leu | Lys | Val | Gly | Val | Ala | |
| | | 610 | | | | | 615 | | | | | 620 | | | | |

| ATG | AGA | TTC | AGC | CCT | GTG | GAG | GTG | GCC | AAG | GCT | GTG | TAC | CGG | TGC | TGG | 1919 |
| Met | Arg | Phe | Ser | Pro | Val | Glu | Val | Ala | Lys | Ala | Val | Tyr | Arg | Cys | Trp | |
| | 625 | | | | | 630 | | | | | 635 | | | | | |

| | | | | | | | | | | | | | | | | |
|---|---|---|---|---|---|---|---|---|---|---|---|---|---|---|---|---|
| GAA | GAG | AAG | CCC | AGT | GCC | CTG | GAA | GCT | GGG | GAC | GCC | ACC | GTC | TGT | CTC | 1967 |
| Glu | Glu | Lys | Pro | Ser | Ala | Leu | Glu | Ala | Gly | Asp | Ala | Thr | Val | Cys | Leu | |
| 640 | | | | 645 | | | | | 650 | | | | | 655 | | |
| ACC | ATC | CAG | AAA | AGC | TCA | CTG | GAC | CAG | CTA | GGT | GAC | ATC | CAA | AGC | TCT | 2015 |
| Thr | Ile | Gln | Lys | Ser | Ser | Leu | Asp | Gln | Leu | Gly | Asp | Ile | Gln | Ser | Ser | |
| | | | | 660 | | | | | 665 | | | | | 670 | | |
| GTC | AGG | TTT | GAT | CTG | GCA | CTG | GAC | CCA | GGT | CGT | CTG | ACT | TCT | CGT | GCC | 2063 |
| Val | Arg | Phe | Asp | Leu | Ala | Leu | Asp | Pro | Gly | Arg | Leu | Thr | Ser | Arg | Ala | |
| | | | 675 | | | | | 680 | | | | | 685 | | | |
| ATT | TTC | AAT | GAA | ACC | AAG | AAC | CCC | ACT | TTG | ACT | CGA | AGA | AAA | ACC | CTG | 2111 |
| Ile | Phe | Asn | Glu | Thr | Lys | Asn | Pro | Thr | Leu | Thr | Arg | Arg | Lys | Thr | Leu | |
| | | | 690 | | | | | 695 | | | | | 700 | | | |
| GGA | CTG | GGG | ATT | CAC | TGT | GAA | ACC | CTG | AAG | CTG | CTT | TTG | CCA | GAT | TGT | 2159 |
| Gly | Leu | Gly | Ile | His | Cys | Glu | Thr | Leu | Lys | Leu | Leu | Leu | Pro | Asp | Cys | |
| | | 705 | | | | | 710 | | | | | 715 | | | | |
| GTG | GAG | GAT | GTG | GTG | AGC | CCC | ATC | ATT | CTG | CAC | CTC | AAC | TTC | TCA | CTG | 2207 |
| Val | Glu | Asp | Val | Val | Ser | Pro | Ile | Ile | Leu | His | Leu | Asn | Phe | Ser | Leu | |
| 720 | | | | | 725 | | | | | 730 | | | | | 735 | |
| GTG | AGA | GAG | CCC | ATC | CCC | TCC | CCC | CAG | AAC | CTG | CGT | CCT | GTG | CTG | GCC | 2255 |
| Val | Arg | Glu | Pro | Ile | Pro | Ser | Pro | Gln | Asn | Leu | Arg | Pro | Val | Leu | Ala | |
| | | | | 740 | | | | | 745 | | | | | 750 | | |
| GTG | GGC | TCA | CAA | GAC | CTC | TTC | ACT | GCT | TCT | CTC | CCC | TTC | GAG | AAG | AAC | 2303 |
| Val | Gly | Ser | Gln | Asp | Leu | Phe | Thr | Ala | Ser | Leu | Pro | Phe | Glu | Lys | Asn | |
| | | | | 755 | | | | | 760 | | | | | 765 | | |
| TGT | GGG | CAA | GAT | GGC | CTC | TGT | GAA | GGG | GAC | CTG | GGT | GTC | ACC | CTC | AGC | 2351 |
| Cys | Gly | Gln | Asp | Gly | Leu | Cys | Glu | Gly | Asp | Leu | Gly | Val | Thr | Leu | Ser | |
| | | 770 | | | | | 775 | | | | | 780 | | | | |
| TTC | TCA | GGC | CTG | CAG | ACC | CTG | ACC | GTG | GGG | AGC | TCC | CTG | GAG | CTC | AAC | 2399 |
| Phe | Ser | Gly | Leu | Gln | Thr | Leu | Thr | Val | Gly | Ser | Ser | Leu | Glu | Leu | Asn | |
| | 785 | | | | | 790 | | | | | 795 | | | | | |
| GTG | ATT | GTG | ACT | GTG | TGG | AAC | GCA | GGT | GAG | GAT | TCC | TAC | GGA | ACC | GTG | 2447 |
| Val | Ile | Val | Thr | Val | Trp | Asn | Ala | Gly | Glu | Asp | Ser | Tyr | Gly | Thr | Val | |
| 800 | | | | | 805 | | | | | 810 | | | | | 815 | |
| GTC | AGC | CTC | TAC | TAT | CCA | GCA | GGG | CTG | TCG | CAC | CGA | CGG | GTG | TCA | GGA | 2495 |
| Val | Ser | Leu | Tyr | Tyr | Pro | Ala | Gly | Leu | Ser | His | Arg | Arg | Val | Ser | Gly | |
| | | | | 820 | | | | | 825 | | | | | 830 | | |
| GCC | CAG | AAG | CAG | CCC | CAT | CAG | AGT | GCC | CTG | CGC | CTG | GCA | TGT | GAG | ACA | 2543 |
| Ala | Gln | Lys | Gln | Pro | His | Gln | Ser | Ala | Leu | Arg | Leu | Ala | Cys | Glu | Thr | |
| | | | 835 | | | | | 840 | | | | | 845 | | | |
| GTG | CCC | ACT | GAG | GAT | GAG | GGC | CTA | AGA | AGC | AGC | CGC | TGC | AGT | GTC | AAC | 2591 |
| Val | Pro | Thr | Glu | Asp | Glu | Gly | Leu | Arg | Ser | Ser | Arg | Cys | Ser | Val | Asn | |
| | | 850 | | | | | 855 | | | | | 860 | | | | |
| CAC | CCC | ATC | TTC | CAT | GAG | GGC | TCT | AAC | GGC | ACC | TTC | ATA | GTC | ACA | TTC | 2639 |
| His | Pro | Ile | Phe | His | Glu | Gly | Ser | Asn | Gly | Thr | Phe | Ile | Val | Thr | Phe | |
| | 865 | | | | | 870 | | | | | 875 | | | | | |
| GAT | GTC | TCC | TAC | AAG | GCC | ACC | CTG | GGA | GAC | AGG | ATG | CTT | ATG | AGG | GCC | 2687 |
| Asp | Val | Ser | Tyr | Lys | Ala | Thr | Leu | Gly | Asp | Arg | Met | Leu | Met | Arg | Ala | |
| 880 | | | | | 885 | | | | | 890 | | | | | 895 | |
| AGT | GCA | AGC | AGT | GAG | AAC | AAT | AAG | GCT | TCA | AGC | AGC | AAG | GCC | ACC | TTC | 2735 |
| Ser | Ala | Ser | Ser | Glu | Asn | Asn | Lys | Ala | Ser | Ser | Ser | Lys | Ala | Thr | Phe | |
| | | | | 900 | | | | | 905 | | | | | 910 | | |
| CAG | CTG | GAG | CTC | CCG | GTG | AAG | TAT | GCA | GTC | TAC | ACC | ATG | ATC | AGC | AGG | 2783 |
| Gln | Leu | Glu | Leu | Pro | Val | Lys | Tyr | Ala | Val | Tyr | Thr | Met | Ile | Ser | Arg | |
| | | | | 915 | | | | | 920 | | | | | 925 | | |
| CAG | GAA | GAA | TCC | ACC | AAG | TAC | TTC | AAC | TTT | GCA | ACC | TCC | GAT | GAG | AAG | 2831 |
| Gln | Glu | Glu | Ser | Thr | Lys | Tyr | Phe | Asn | Phe | Ala | Thr | Ser | Asp | Glu | Lys | |
| | | 930 | | | | | 935 | | | | | 940 | | | | |
| AAA | ATG | AAA | GAG | GCT | GAG | CAT | CGA | TAC | CGT | GTG | AAT | AAC | CTC | AGC | CAG | 2879 |
| Lys | Met | Lys | Glu | Ala | Glu | His | Arg | Tyr | Arg | Val | Asn | Asn | Leu | Ser | Gln | |
| | 945 | | | | | 950 | | | | | 955 | | | | | |
| CGA | GAT | CTG | GCC | ATC | AGC | ATT | AAC | TTC | TGG | GTT | CCT | GTC | CTG | CTG | AAC | 2927 |

|  |  |  |  |  |  |  |  |  |  |  |  |  |  |  |  |
|---|---|---|---|---|---|---|---|---|---|---|---|---|---|---|---|
| Arg | Asp | Leu | Ala | Ile | Ser | Ile | Asn | Phe | Trp | Val | Pro | Val | Leu | Leu | Asn |
| 960 |  |  |  |  | 965 |  |  |  | 970 |  |  |  |  |  | 975 |

```
GGG GTG GCT GTG TGG GAT GTG GTC ATG GAG GCC CCA TCT CAG AGT CTC         2975
Gly Val Ala Val Trp Asp Val Val Met Glu Ala Pro Ser Gln Ser Leu
            980                 985                 990

CCC TGT GTT TCA GAG AGA AAA CCT CCC CAG CAT TCT GAC TTC CTG ACC         3023
Pro Cys Val Ser Glu Arg Lys Pro Pro Gln His Ser Asp Phe Leu Thr
                995                 1000                1005

CAG ATT TCA AGA AGT CCC ATG CTG GAC TGC TCC ATT GCT GAC TGC CTG         3071
Gln Ile Ser Arg Ser Pro Met Leu Asp Cys Ser Ile Ala Asp Cys Leu
            1010                1015                1020

CAG TTC CGC TGT GAC GTC CCC TCC TTC AGC GTC CAG GAG GAG CTG GAT         3119
Gln Phe Arg Cys Asp Val Pro Ser Phe Ser Val Gln Glu Glu Leu Asp
        1025                1030                1035

TTC ACC CTG AAG GGC AAT CTC AGT TTC GGC TGG GTC CGC GAG ACA TTG         3167
Phe Thr Leu Lys Gly Asn Leu Ser Phe Gly Trp Val Arg Glu Thr Leu
1040                1045                1050                1055

CAG AAG AAG GTG TTG GTC GTG AGT GTG GCT GAA ATT ACG TTC GAC ACA         3215
Gln Lys Lys Val Leu Val Val Ser Val Ala Glu Ile Thr Phe Asp Thr
                1060                1065                1070

TCC GTG TAC TCC CAG CTT CCA GGA CAG GAG GCA TTT ATG AGA GCT CAG         3263
Ser Val Tyr Ser Gln Leu Pro Gly Gln Glu Ala Phe Met Arg Ala Gln
            1075                1080                1085

ATG GAG ATG GTG CTA GAA GAA GAC GAG GTC TAC AAT GCC ATT CCC ATC         3311
Met Glu Met Val Leu Glu Glu Asp Glu Val Tyr Asn Ala Ile Pro Ile
        1090                1095                1100

ATC ATG GGC AGC TCT GTG GGG GCT CTG CTA CTG CTG GCG CTC ATC ACA         3359
Ile Met Gly Ser Ser Val Gly Ala Leu Leu Leu Leu Ala Leu Ile Thr
1105                1110                1115

GCC ACA CTG TAC AAG CTT GGC TTC TTC AAA CGC CAC TAC AAG GAA ATG         3407
Ala Thr Leu Tyr Lys Leu Gly Phe Phe Lys Arg His Tyr Lys Glu Met
1120                1125                1130                1135

CTG GAG GAC AAG CCT GAA GAC ACT GCC ACA TTC AGT GGG GAC GAT TTC         3455
Leu Glu Asp Lys Pro Glu Asp Thr Ala Thr Phe Ser Gly Asp Asp Phe
                1140                1145                1150

AGC TGT GTG GCC CCA AAT GTG CCT TTG TCC TAATAATCCA CTTTCCTGTT           3505
Ser Cys Val Ala Pro Asn Val Pro Leu Ser
            1155                1160

TATCTCTACC ACTGTGGGCT GGACTTGCTT GCAACCATAA ATCAACTTAC ATGGAAACAA       3565

CTTCTGCATA GATCTGCACT GGCCTAAGCA ACCTACCAGG TGCTAAGCAC CTTCTCGGAG       3625

AGATAGAGAT TGTAATGTTT TTACATATCT GTCCATCTTT TTCAGCAATG ACCCACTTTT       3685

TACAGAAGCA GGCATGGTGC CAGCATAAAT TTTCATATGC T                          3726
```

( 2 ) INFORMATION FOR SEQ ID NO:2:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr Phe Gly Thr Val Leu Leu Leu Ser Val Leu Ala Ser Tyr His Gly
 1               5                   10                  15

Phe Asn Leu Asp Val Glu Glu Pro Thr Ile Phe Gln Glu Asp Ala Gly
                20                  25                  30

Gly Phe Gly Gln Ser Val Val Gln Phe Gly Gly Ser Arg Leu Val Val
            35                  40                  45

Gly Ala Pro Leu Glu Val Val Ala Ala Asn Gln Thr Gly Arg Leu Tyr
        50                  55                  60
```

```
Asp Cys Ala Ala Ala Thr Gly Met Cys Gln Pro Ile Pro Leu His Ile
 65                  70                  75                  80

Arg Pro Glu Ala Val Asn Met Ser Leu Gly Leu Thr Leu Ala Ala Ser
                 85                  90                  95

Thr Asn Gly Ser Arg Leu Leu Ala Cys Gly Pro Thr Leu His Arg Val
            100                 105                 110

Cys Gly Glu Asn Ser Tyr Ser Lys Gly Ser Cys Leu Leu Leu Gly Ser
        115                 120                 125

Arg Trp Glu Ile Ile Gln Thr Val Pro Asp Ala Thr Pro Glu Cys Pro
    130                 135                 140

His Gln Glu Met Asp Ile Val Phe Leu Ile Asp Gly Ser Gly Ser Ile
145                 150                 155                 160

Asp Gln Asn Asp Phe Asn Gln Met Lys Gly Phe Val Gln Ala Val Met
                165                 170                 175

Gly Gln Phe Glu Gly Thr Asp Thr Leu Phe Ala Leu Met Gln Tyr Ser
            180                 185                 190

Asn Leu Leu Lys Ile His Phe Thr Phe Thr Gln Phe Arg Thr Ser Pro
        195                 200                 205

Ser Gln Gln Ser Leu Val Asp Pro Ile Val Gln Leu Lys Gly Leu Thr
    210                 215                 220

Phe Thr Ala Thr Gly Ile Leu Thr Val Val Thr Gln Leu Phe His His
225                 230                 235                 240

Lys Asn Gly Ala Arg Lys Ser Ala Lys Lys Ile Leu Ile Val Ile Thr
                245                 250                 255

Asp Gly Gln Lys Tyr Lys Asp Pro Leu Glu Tyr Ser Asp Val Ile Pro
            260                 265                 270

Gln Ala Glu Lys Ala Gly Ile Ile Arg Tyr Ala Ile Gly Val Gly His
        275                 280                 285

Ala Phe Gln Gly Pro Thr Ala Arg Gln Glu Leu Asn Thr Ile Ser Ser
    290                 295                 300

Ala Pro Pro Gln Asp His Val Phe Lys Val Asp Asn Phe Ala Ala Leu
305                 310                 315                 320

Gly Ser Ile Gln Lys Gln Leu Gln Glu Lys Ile Tyr Ala Val Glu Gly
                325                 330                 335

Thr Gln Ser Arg Ala Ser Ser Ser Phe Gln His Glu Met Ser Gln Glu
            340                 345                 350

Gly Phe Ser Thr Ala Leu Thr Met Asp Gly Leu Phe Leu Gly Ala Val
        355                 360                 365

Gly Ser Phe Ser Trp Ser Gly Ala Phe Leu Tyr Pro Pro Asn Met
    370                 375                 380

Ser Pro Thr Phe Ile Asn Met Ser Gln Glu Asn Val Asp Met Arg Asp
385                 390                 395                 400

Ser Tyr Leu Gly Tyr Ser Thr Glu Leu Ala Leu Trp Lys Gly Val Gln
                405                 410                 415

Asn Leu Val Leu Gly Ala Pro Arg Tyr Gln His Thr Gly Lys Ala Val
            420                 425                 430

Ile Phe Thr Gln Val Ser Arg Gln Trp Arg Lys Lys Ala Glu Val Thr
        435                 440                 445

Gly Thr Gln Ile Gly Ser Tyr Phe Gly Ala Ser Leu Cys Ser Val Asp
    450                 455                 460

Val Asp Ser Asp Gly Ser Thr Asp Leu Ile Leu Ile Gly Ala Pro His
465                 470                 475                 480

Tyr Tyr Glu Gln Thr Arg Gly Gly Gln Val Ser Val Cys Pro Leu Pro
                485                 490                 495
```

```
Arg Gly Gln Arg Val Gln Trp Gln Cys Asp Ala Val Leu Arg Gly Glu
            500                 505                 510

Gln Gly His Pro Trp Gly Arg Phe Gly Ala Ala Leu Thr Val Leu Gly
        515                 520                 525

Asp Val Asn Glu Asp Lys Leu Ile Asp Val Ala Ile Gly Ala Pro Gly
        530                 535                 540

Glu Gln Glu Asn Arg Gly Ala Val Tyr Leu Phe His Gly Ala Ser Glu
545                 550                 555                 560

Ser Gly Ile Ser Pro Ser His Ser Gln Arg Ile Ala Ser Ser Gln Leu
            565                 570                 575

Ser Pro Arg Leu Gln Tyr Phe Gly Gln Ala Leu Ser Gly Gly Gln Asp
        580                 585                 590

Leu Thr Gln Asp Gly Leu Met Asp Leu Ala Val Gly Ala Arg Gly Gln
        595                 600                 605

Val Leu Leu Leu Arg Ser Leu Pro Val Leu Lys Val Gly Val Ala Met
610                 615                 620

Arg Phe Ser Pro Val Glu Val Ala Lys Ala Val Tyr Arg Cys Trp Glu
625                 630                 635                 640

Glu Lys Pro Ser Ala Leu Glu Ala Gly Asp Ala Thr Val Cys Leu Thr
            645                 650                 655

Ile Gln Lys Ser Ser Leu Asp Gln Leu Gly Asp Ile Gln Ser Ser Val
            660                 665                 670

Arg Phe Asp Leu Ala Leu Asp Pro Gly Arg Leu Thr Ser Arg Ala Ile
        675                 680                 685

Phe Asn Glu Thr Lys Asn Pro Thr Leu Thr Arg Arg Lys Thr Leu Gly
        690                 695                 700

Leu Gly Ile His Cys Glu Thr Leu Lys Leu Leu Leu Pro Asp Cys Val
705                 710                 715                 720

Glu Asp Val Val Ser Pro Ile Ile Leu His Leu Asn Phe Ser Leu Val
            725                 730                 735

Arg Glu Pro Ile Pro Ser Pro Gln Asn Leu Arg Pro Val Leu Ala Val
            740                 745                 750

Gly Ser Gln Asp Leu Phe Thr Ala Ser Leu Pro Phe Glu Lys Asn Cys
        755                 760                 765

Gly Gln Asp Gly Leu Cys Glu Gly Asp Leu Gly Val Thr Leu Ser Phe
        770                 775                 780

Ser Gly Leu Gln Thr Leu Thr Val Gly Ser Ser Leu Glu Leu Asn Val
785                 790                 795                 800

Ile Val Thr Val Trp Asn Ala Gly Glu Asp Ser Tyr Gly Thr Val Val
            805                 810                 815

Ser Leu Tyr Tyr Pro Ala Gly Leu Ser His Arg Arg Val Ser Gly Ala
            820                 825                 830

Gln Lys Gln Pro His Gln Ser Ala Leu Arg Leu Ala Cys Glu Thr Val
        835                 840                 845

Pro Thr Glu Asp Glu Gly Leu Arg Ser Ser Arg Cys Ser Val Asn His
    850                 855                 860

Pro Ile Phe His Glu Gly Ser Asn Gly Thr Phe Ile Val Thr Phe Asp
865                 870                 875                 880

Val Ser Tyr Lys Ala Thr Leu Gly Asp Arg Met Leu Met Arg Ala Ser
                885                 890                 895

Ala Ser Ser Glu Asn Asn Lys Ala Ser Ser Ser Lys Ala Thr Phe Gln
            900                 905                 910

Leu Glu Leu Pro Val Lys Tyr Ala Val Tyr Thr Met Ile Ser Arg Gln
        915                 920                 925

Glu Glu Ser Thr Lys Tyr Phe Asn Phe Ala Thr Ser Asp Glu Lys Lys
```

|   | 930 |   |   |   | 935 |   |   |   | 940 |   |   |
|---|---|---|---|---|---|---|---|---|---|---|---|

Met Lys Glu Ala Glu His Arg Tyr Arg Val Asn Asn Leu Ser Gln Arg
945     950     955     960

Asp Leu Ala Ile Ser Ile Asn Phe Trp Val Pro Val Leu Leu Asn Gly
     965     970     975

Val Ala Val Trp Asp Val Val Met Glu Ala Pro Ser Gln Ser Leu Pro
   980     985     990

Cys Val Ser Glu Arg Lys Pro Pro Gln His Ser Asp Phe Leu Thr Gln
  995     1000     1005

Ile Ser Arg Ser Pro Met Leu Asp Cys Ser Ile Ala Asp Cys Leu Gln
  1010     1015     1020

Phe Arg Cys Asp Val Pro Ser Phe Ser Val Gln Glu Glu Leu Asp Phe
1025     1030     1035     1040

Thr Leu Lys Gly Asn Leu Ser Phe Gly Trp Val Arg Glu Thr Leu Gln
     1045     1050     1055

Lys Lys Val Leu Val Val Ser Val Ala Glu Ile Thr Phe Asp Thr Ser
     1060     1065     1070

Val Tyr Ser Gln Leu Pro Gly Gln Glu Ala Phe Met Arg Ala Gln Met
     1075     1080     1085

Glu Met Val Leu Glu Glu Asp Glu Val Tyr Asn Ala Ile Pro Ile Ile
  1090     1095     1100

Met Gly Ser Ser Val Gly Ala Leu Leu Leu Leu Ala Leu Ile Thr Ala
1105     1110     1115     1120

Thr Leu Tyr Lys Leu Gly Phe Phe Lys Arg His Tyr Lys Glu Met Leu
     1125     1130     1135

Glu Asp Lys Pro Glu Asp Thr Ala Thr Phe Ser Gly Asp Asp Phe Ser
     1140     1145     1150

Cys Val Ala Pro Asn Val Pro Lys Ser
     1155     1160

( 2 ) INFORMATION FOR SEQ ID NO:3:

( i ) SEQUENCE CHARACTERISTICS:
  ( A ) LENGTH: 1153 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:3:

Met Ala Leu Arg Val Leu Leu Leu Thr Ala Leu Thr Leu Cys His Gly
1    5     10     15

Phe Asn Leu Asp Thr Glu Asn Ala Met Thr Phe Gln Glu Asn Ala Arg
    20     25     30

Gly Phe Gly Gln Ser Val Val Gln Leu Gln Gly Ser Arg Val Val Val
   35     40     45

Gly Ala Pro Gln Glu Ile Val Ala Ala Asn Gln Arg Gly Ser Leu Tyr
  50     55     60

Gln Cys Asp Tyr Ser Thr Gly Ser Cys Glu Pro Ile Arg Leu Gln Val
65     70     75     80

Pro Val Glu Ala Val Asn Met Ser Leu Gly Leu Ser Leu Ala Ala Thr
    85     90     95

Thr Ser Pro Pro Gln Leu Leu Ala Cys Gly Pro Thr Val His Gln Thr
     100     105     110

Cys Ser Glu Asn Thr Tyr Val Lys Gly Leu Cys Phe Leu Phe Gly Ser
   115     120     125

Asn Leu Arg Gln Gln Pro Gln Lys Phe Pro Glu Ala Leu Arg Gly Cys

```
                    130                     135                         140

Pro  Gln  Glu  Asp  Ser  Asp  Ile  Ala  Phe  Leu  Ile  Asp  Gly  Ser  Gly  Ser
145                      150                      155                      160

Ile  Ile  Pro  His  Asp  Phe  Arg  Arg  Met  Lys  Glu  Phe  Val  Ser  Thr  Val
                    165                      170                      175

Met  Glu  Gln  Leu  Lys  Lys  Ser  Lys  Thr  Leu  Phe  Ser  Leu  Met  Gln  Tyr
               180                      185                      190

Ser  Glu  Glu  Phe  Arg  Ile  His  Phe  Thr  Phe  Lys  Glu  Phe  Gln  Asn  Asn
          195                      200                      205

Pro  Asn  Pro  Arg  Ser  Leu  Val  Lys  Pro  Ile  Thr  Gln  Leu  Leu  Gly  Arg
     210                      215                      220

Thr  His  Thr  Ala  Thr  Gly  Ile  Arg  Lys  Val  Val  Arg  Glu  Leu  Phe  Asn
225                      230                      235                      240

Ile  Thr  Asn  Gly  Ala  Arg  Lys  Asn  Ala  Phe  Lys  Ile  Leu  Val  Val  Ile
                    245                      250                      255

Thr  Asp  Gly  Glu  Lys  Phe  Gly  Asp  Pro  Leu  Gly  Tyr  Glu  Asp  Val  Ile
                    260                      265                      270

Pro  Glu  Ala  Asp  Arg  Glu  Gly  Val  Ile  Arg  Tyr  Val  Ile  Gly  Val  Gly
               275                      280                      285

Asp  Ala  Phe  Arg  Ser  Glu  Lys  Ser  Arg  Gln  Glu  Leu  Asn  Thr  Ile  Ala
          290                      295                      300

Ser  Lys  Pro  Pro  Arg  Asp  His  Val  Phe  Gln  Val  Asn  Asn  Phe  Glu  Ala
305                      310                      315                      320

Leu  Lys  Thr  Ile  Gln  Asn  Gln  Leu  Arg  Glu  Lys  Ile  Phe  Ala  Ile  Glu
                    325                      330                      335

Gly  Thr  Gln  Thr  Gly  Ser  Ser  Ser  Phe  Glu  His  Glu  Met  Ser  Gln
                    340                      345                      350

Glu  Gly  Phe  Ser  Ala  Ala  Ile  Thr  Ser  Asn  Gly  Pro  Leu  Leu  Ser  Thr
               355                      360                      365

Val  Gly  Ser  Tyr  Asp  Trp  Ala  Gly  Gly  Val  Phe  Leu  Tyr  Thr  Ser  Lys
     370                      375                      380

Glu  Lys  Ser  Thr  Phe  Ile  Asn  Met  Thr  Arg  Val  Asp  Ser  Asp  Met  Asn
385                      390                      395                      400

Asp  Ala  Tyr  Leu  Gly  Tyr  Ala  Ala  Ala  Ile  Ile  Leu  Arg  Asn  Arg  Val
                    405                      410                      415

Gln  Ser  Leu  Val  Leu  Gly  Ala  Pro  Arg  Tyr  Gln  His  Ile  Gly  Leu  Val
               420                      425                      430

Ala  Met  Phe  Arg  Gln  Asn  Thr  Gly  Met  Trp  Glu  Ser  Asn  Ala  Asn  Val
          435                      440                      445

Lys  Gly  Thr  Gln  Ile  Gly  Ala  Tyr  Phe  Gly  Ala  Ser  Leu  Cys  Ser  Val
     450                      455                      460

Asp  Val  Asp  Ser  Asn  Gly  Ser  Thr  Asp  Leu  Val  Leu  Ile  Gly  Ala  Pro
465                      470                      475                      480

His  Tyr  Tyr  Glu  Gln  Thr  Arg  Gly  Gly  Gln  Val  Ser  Val  Cys  Pro  Leu
                    485                      490                      495

Pro  Arg  Gly  Gln  Arg  Ala  Arg  Trp  Gln  Cys  Asp  Ala  Val  Leu  Tyr  Gly
               500                      505                      510

Glu  Gln  Gly  Gln  Pro  Trp  Gly  Arg  Phe  Gly  Ala  Ala  Leu  Thr  Val  Leu
          515                      520                      525

Gly  Asp  Val  Asn  Gly  Asp  Lys  Leu  Thr  Asp  Val  Ala  Ile  Gly  Ala  Pro
     530                      535                      540

Gly  Glu  Glu  Asp  Asn  Arg  Gly  Ala  Val  Tyr  Leu  Phe  His  Gly  Thr  Ser
545                      550                      555                      560

Gly  Ser  Gly  Ile  Ser  Pro  Ser  His  Ser  Gln  Arg  Ile  Ala  Gly  Ser  Lys
                    565                      570                      575
```

-continued

| | | | | | | | | | | | | | | |
|---|---|---|---|---|---|---|---|---|---|---|---|---|---|---|
|Leu|Ser|Pro|Arg 580|Leu|Gln|Tyr|Phe|Gly 585|Gln|Ser|Leu|Ser 590|Gly|Gly|Gln|
|Asp|Leu|Thr 595|Met|Asp|Gly|Leu|Val 600|Asp|Leu|Thr|Val 605|Gly|Ala|Gln|Gly|
|His|Val 610|Leu|Leu|Leu|Arg|Ser 615|Gln|Pro|Val|Leu|Arg 620|Val|Lys|Ala|Ile|
|Met 625|Glu|Phe|Asn|Pro|Arg 630|Glu|Val|Ala|Arg|Asn 635|Val|Phe|Glu|Cys|Asn 640|
|Asp|Gln|Val|Val|Lys 645|Gly|Lys|Glu|Ala|Gly 650|Glu|Val|Arg|Val|Cys 655|Leu|
|His|Val|Gln|Lys 660|Ser|Thr|Arg|Asp|Arg 665|Leu|Arg|Glu|Gly|Gln 670|Ile|Gln|
|Ser|Val|Val 675|Thr|Tyr|Asp|Leu|Ala 680|Leu|Asp|Ser|Gly|Arg 685|Pro|His|Ser|
|Arg|Ala 690|Val|Phe|Asn|Glu|Thr 695|Lys|Asn|Ser|Thr|Arg 700|Arg|Gln|Thr|Gln|
|Val 705|Leu|Gly|Leu|Thr|Gln 710|Thr|Cys|Glu|Thr|Leu 715|Lys|Leu|Gln|Leu|Pro 720|
|Asn|Cys|Ile|Glu|Asp 725|Pro|Val|Ser|Pro|Ile 730|Val|Leu|Arg|Leu|Asn 735|Phe|
|Ser|Leu|Val|Gly 740|Thr|Pro|Leu|Ser|Ala 745|Phe|Gly|Asn|Leu|Arg 750|Pro|Val|
|Leu|Ala|Glu|Asp 755|Ala|Gln|Arg|Leu|Phe 760|Thr|Ala|Leu|Phe 765|Pro|Phe|Glu|
|Lys|Asn 770|Cys|Gly|Asn|Asp|Asn 775|Ile|Cys|Gln|Asp|Asp 780|Leu|Ser|Ile|Thr|
|Phe 785|Ser|Phe|Met|Ser|Leu 790|Asp|Cys|Leu|Val|Val 795|Gly|Gly|Pro|Arg|Glu 800|
|Phe|Asn|Val|Thr 805|Val|Thr|Val|Arg|Asn 810|Asp|Gly|Glu|Asp|Ser 815|Tyr|Arg|
|Thr|Gln|Val|Thr 820|Phe|Phe|Phe|Pro|Leu 825|Asp|Leu|Ser|Tyr|Arg 830|Lys|Val|
|Ser|Thr|Leu 835|Gln|Asn|Gln|Arg|Ser 840|Gln|Arg|Ser|Trp|Arg 845|Leu|Ala|Cys|
|Glu|Ser 850|Ala|Ser|Ser|Thr|Glu 855|Val|Ser|Gly|Ala|Leu 860|Lys|Ser|Thr|Ser|
|Cys 865|Ser|Ile|Asn|His|Pro 870|Ile|Phe|Pro|Glu|Asn 875|Ser|Glu|Val|Thr|Phe 880|
|Asn|Ile|Thr|Phe|Asp 885|Val|Asp|Ser|Lys|Ala 890|Ser|Leu|Gly|Asn|Lys 895|Leu|
|Leu|Leu|Lys|Ala 900|Asn|Val|Thr|Ser|Glu 905|Asn|Asn|Met|Pro|Arg 910|Thr|Asn|
|Lys|Thr|Glu 915|Phe|Gln|Leu|Glu|Leu 920|Pro|Val|Lys|Tyr|Ala 925|Val|Tyr|Met|
|Val|Val 930|Thr|Ser|His|Gly|Val 935|Ser|Thr|Lys|Tyr|Leu 940|Asn|Phe|Thr|Ala|
|Ser 945|Glu|Asn|Thr|Ser|Arg 950|Val|Met|Gln|His|Gln 955|Tyr|Gln|Val|Ser|Asn 960|
|Leu|Gly|Gln|Arg|Ser 965|Leu|Pro|Ile|Ser|Leu 970|Val|Phe|Leu|Val|Pro 975|Val|
|Arg|Leu|Asn|Gln 980|Thr|Val|Ile|Trp|Asp 985|Arg|Pro|Gln|Val|Thr 990|Phe|Ser|
|Glu|Asn|Leu 995|Ser|Ser|Thr|Cys|His 1000|Thr|Lys|Glu|Arg|Leu 1005|Pro|Ser|His|

|     |     |     |     |     |     |     |     |     |     |     |     |     |     |     |
|-----|-----|-----|-----|-----|-----|-----|-----|-----|-----|-----|-----|-----|-----|-----|
| Ser | Asp | Phe | Leu | Ala | Glu | Leu | Arg | Lys | Ala | Pro | Val | Val | Asn | Cys | Ser |
|     | 1010 |   |   |   | 1015 |   |   |   | 1020 |   |   |   |   |   |
| Ile | Ala | Val | Cys | Gln | Arg | Ile | Gln | Cys | Asp | Ile | Pro | Phe | Phe | Gly | Ile |
| 1025 |   |   |   | 1030 |   |   |   | 1035 |   |   |   |   |   | 1040 |
| Gln | Glu | Glu | Phe | Asn | Ala | Thr | Leu | Lys | Gly | Asn | Leu | Ser | Phe | Asp | Trp |
|   |   |   | 1045 |   |   |   | 1050 |   |   |   |   | 1055 |   |   |
| Tyr | Ile | Lys | Thr | Ser | His | Asn | His | Leu | Ile | Val | Ser | Thr | Ala | Glu |
|   |   |   | 1060 |   |   |   | 1065 |   |   |   | 1070 |   |   |
| Ile | Leu | Phe | Asn | Asp | Ser | Val | Phe | Thr | Leu | Leu | Pro | Gly | Gln | Gly | Ala |
|   |   | 1075 |   |   |   | 1080 |   |   |   | 1085 |   |   |   |   |
| Phe | Val | Arg | Ser | Gln | Thr | Glu | Thr | Lys | Val | Glu | Pro | Phe | Glu | Val | Pro |
|   | 1090 |   |   |   | 1095 |   |   |   | 1100 |   |   |   |   |   |
| Asn | Pro | Leu | Pro | Leu | Ile | Val | Gly | Ser | Ser | Val | Gly | Gly | Leu | Leu | Leu |
| 1105 |   |   |   | 1110 |   |   |   | 1115 |   |   |   |   |   | 1120 |
| Leu | Ala | Leu | Ile | Thr | Ala | Ala | Leu | Tyr | Lys | Leu | Gly | Phe | Phe | Lys | Arg |
|   |   |   |   | 1125 |   |   |   | 1130 |   |   |   |   | 1135 |   |
| Gln | Tyr | Lys | Asp | Met | Met | Ser | Glu | Gly | Gly | Pro | Pro | Gly | Ala | Glu | Pro |
|   |   |   | 1140 |   |   |   | 1145 |   |   |   | 1150 |   |   |
| Gln |     |     |     |     |     |     |     |     |     |     |     |     |     |     |

( 2 ) INFORMATION FOR SEQ ID NO:4:

( i ) SEQUENCE CHARACTERISTICS:
( A ) LENGTH: 1163 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

|     |     |     |     |     |     |     |     |     |     |     |     |     |     |     |
|-----|-----|-----|-----|-----|-----|-----|-----|-----|-----|-----|-----|-----|-----|-----|
| Met | Thr | Arg | Thr | Arg | Ala | Ala | Leu | Leu | Leu | Phe | Thr | Ala | Leu | Ala | Thr |
| 1 |   |   |   | 5 |   |   |   |   | 10 |   |   |   |   | 15 |
| Ser | Leu | Gly | Phe | Asn | Leu | Asp | Thr | Glu | Glu | Leu | Thr | Ala | Phe | Arg | Val |
|   |   |   | 20 |   |   |   |   | 25 |   |   |   |   | 30 |   |
| Asp | Ser | Ala | Gly | Phe | Gly | Asp | Ser | Val | Val | Gln | Tyr | Ala | Asn | Ser | Trp |
|   |   | 35 |   |   |   |   | 40 |   |   |   |   | 45 |   |   |
| Val | Val | Val | Gly | Ala | Pro | Gln | Lys | Ile | Ile | Ala | Ala | Asn | Gln | Ile | Gly |
|   | 50 |   |   |   |   | 55 |   |   |   |   | 60 |   |   |   |   |
| Gly | Leu | Tyr | Gln | Cys | Gly | Tyr | Ser | Thr | Gly | Ala | Cys | Glu | Pro | Ile | Gly |
| 65 |   |   |   |   | 70 |   |   |   |   | 75 |   |   |   |   | 80 |
| Leu | Gln | Val | Pro | Pro | Glu | Ala | Val | Asn | Met | Ser | Leu | Gly | Leu | Ser | Leu |
|   |   |   |   | 85 |   |   |   |   | 90 |   |   |   |   | 95 |   |
| Ala | Ser | Thr | Thr | Ser | Pro | Ser | Gln | Leu | Leu | Ala | Cys | Gly | Pro | Thr | Val |
|   |   |   | 100 |   |   |   |   | 105 |   |   |   |   | 110 |   |
| His | His | Glu | Cys | Gly | Arg | Asn | Met | Tyr | Leu | Thr | Gly | Leu | Cys | Phe | Leu |
|   |   | 115 |   |   |   |   | 120 |   |   |   |   | 125 |   |   |
| Leu | Gly | Pro | Thr | Gln | Leu | Thr | Gln | Arg | Leu | Pro | Val | Ser | Arg | Gln | Glu |
|   | 130 |   |   |   |   | 135 |   |   |   |   | 140. |   |   |   |   |
| Cys | Pro | Arg | Gln | Glu | Gln | Asp | Ile | Val | Phe | Leu | Ile | Asp | Gly | Ser | Gly |
| 145 |   |   |   |   | 150 |   |   |   |   | 155 |   |   |   |   | 160 |
| Ser | Ile | Ser | Ser | Arg | Asn | Phe | Ala | Thr | Met | Met | Asn | Phe | Val | Arg | Ala |
|   |   |   |   | 165 |   |   |   |   | 170 |   |   |   |   | 175 |   |
| Val | Ile | Ser | Gln | Phe | Gln | Arg | Pro | Ser | Thr | Gln | Phe | Ser | Leu | Met | Gln |
|   |   |   | 180 |   |   |   |   | 185 |   |   |   |   | 190 |   |
| Phe | Ser | Asn | Lys | Phe | Gln | Thr | His | Phe | Thr | Phe | Glu | Glu | Phe | Arg | Arg |
|   |   |   | 195 |   |   |   |   | 200 |   |   |   |   | 205 |   |
| Thr | Ser | Asn | Pro | Leu | Ser | Leu | Leu | Ala | Ser | Val | His | Gln | Leu | Gln | Gly |

-continued

```
         210                    215                     220
Phe  Thr  Tyr  Thr  Ala  Thr  Ala  Ile  Gln  Asn  Val  His  Arg  Leu  Phe
225                      230                     235                      240

His  Ala  Ser  Tyr  Gly  Ala  Arg  Arg  Asp  Ala  Ile  Lys  Ile  Leu  Ile  Val
                    245                      250                     255

Ile  Thr  Asp  Gly  Lys  Lys  Glu  Gly  Asp  Ser  Leu  Asp  Tyr  Lys  Asp  Val
                    260                      265                     270

Ile  Pro  Met  Ala  Asp  Ala  Ala  Gly  Ile  Ile  Arg  Tyr  Ala  Ile  Gly  Val
               275                      280                     285

Gly  Leu  Ala  Phe  Gln  Asn  Arg  Asn  Ser  Trp  Lys  Glu  Leu  Asn  Asp  Ile
290                      295                     300

Ala  Ser  Lys  Pro  Ser  Gln  Glu  His  Ile  Phe  Lys  Val  Glu  Asp  Phe  Asp
305                      310                     315                      320

Ala  Leu  Lys  Asp  Ile  Gln  Asn  Gln  Leu  Lys  Glu  Lys  Ile  Phe  Ala  Ile
                    325                      330                     335

Glu  Gly  Thr  Glu  Thr  Ile  Ser  Ser  Ser  Phe  Glu  Leu  Glu  Met  Ala
                    340                      345                     350

Gln  Glu  Gly  Phe  Ser  Ala  Val  Phe  Thr  Pro  Asp  Gly  Pro  Val  Leu  Gly
               355                      360                     365

Ala  Val  Gly  Ser  Phe  Thr  Trp  Ser  Gly  Gly  Ala  Phe  Leu  Tyr  Pro  Pro
370                      375                     380

Asn  Met  Ser  Pro  Thr  Phe  Ile  Asn  Met  Ser  Gln  Glu  Asn  Val  Asp  Met
385                      390                     395                      400

Arg  Asp  Ser  Tyr  Leu  Gly  Tyr  Ser  Thr  Glu  Leu  Ala  Leu  Trp  Lys  Gly
                    405                      410                     415

Val  Gln  Ser  Leu  Val  Leu  Gly  Ala  Pro  Arg  Tyr  Gln  His  Ile  Gly  Lys
                    420                      425                     430

Ala  Val  Ile  Phe  Ile  Gln  Val  Ser  Arg  Gln  Trp  Arg  Met  Lys  Ala  Glu
               435                      440                     445

Val  Ile  Gly  Thr  Gln  Ile  Gly  Ser  Tyr  Phe  Gly  Ala  Ser  Leu  Cys  Ser
               450                      455                     460

Val  Asp  Val  Asp  Thr  Asp  Gly  Ser  Thr  Asp  Leu  Val  Leu  Ile  Gly  Ala
465                      470                     475                      480

Pro  His  Tyr  Tyr  Glu  Gln  Thr  Arg  Gly  Gly  Gln  Val  Ser  Val  Cys  Pro
                    485                      490                     495

Leu  Pro  Arg  Gly  Trp  Arg  Arg  Trp  Trp  Cys  Asp  Ala  Val  Leu  Tyr  Gly
               500                      505                     510

Glu  Gln  Gly  His  Pro  Trp  Gly  Arg  Phe  Gly  Ala  Ala  Leu  Thr  Val  Leu
               515                      520                     525

Gly  Asp  Val  Asn  Gly  Asp  Lys  Leu  Thr  Asp  Val  Val  Ile  Gly  Ala  Pro
530                      535                     540

Gly  Glu  Glu  Glu  Asn  Arg  Gly  Ala  Val  Tyr  Leu  Phe  His  Gly  Val  Leu
545                      550                     555                      560

Gly  Pro  Ser  Ile  Ser  Pro  Ser  His  Ser  Gln  Arg  Ile  Ala  Gly  Ser  Gln
                    565                      570                     575

Leu  Ser  Ser  Arg  Leu  Gln  Tyr  Phe  Gly  Gln  Ala  Leu  Ser  Gly  Gly  Gln
                    580                      585                     590

Asp  Leu  Thr  Gln  Asp  Gly  Leu  Val  Asp  Leu  Ala  Val  Gly  Ala  Arg  Gly
          595                      600                     605

Gln  Val  Leu  Leu  Leu  Arg  Thr  Arg  Pro  Val  Leu  Trp  Val  Gly  Val  Ser
610                      615                     620

Met  Gln  Phe  Ile  Pro  Ala  Glu  Ile  Pro  Arg  Ser  Ala  Phe  Glu  Cys  Arg
625                      630                     635                      640

Glu  Gln  Val  Val  Ser  Glu  Gln  Thr  Leu  Val  Gln  Ser  Asn  Ile  Cys  Leu
                    645                      650                     655
```

```
Tyr Ile Asp Lys Arg Ser Lys Asn Leu Leu Gly Ser Arg Asp Leu Gln
            660                 665                 670

Ser Ser Val Thr Leu Asp Leu Ala Leu Ala Pro Gly Arg Leu Ser Pro
        675                 680                 685

Arg Ala Ile Phe Gln Glu Thr Lys Asn Arg Ser Leu Ser Arg Val Arg
        690                 695                 700

Val Leu Gly Leu Lys Ala His Cys Glu Asn Phe Asn Leu Leu Leu Pro
705                 710                 715                 720

Ser Cys Val Glu Asp Ser Val Ile Pro Ile Leu Arg Leu Asn Phe
                725                 730                 735

Thr Leu Val Gly Lys Pro Leu Leu Ala Phe Arg Asn Leu Arg Pro Met
            740                 745                 750

Leu Ala Ala Leu Ala Gln Arg Tyr Phe Thr Ala Ser Leu Pro Phe Glu
            755                 760                 765

Lys Asn Cys Gly Ala Asp His Ile Cys Gln Asp Asn Leu Gly Ile Ser
            770                 775                 780

Phe Ser Phe Pro Gly Leu Lys Ser Leu Leu Val Gly Ser Asn Leu Glu
785                 790                 795                 800

Leu Asn Ala Glu Val Met Val Trp Asn Asp Gly Glu Asp Ser Tyr Gly
                805                 810                 815

Thr Thr Ile Thr Phe Ser His Pro Ala Gly Leu Ser Tyr Arg Tyr Val
            820                 825                 830

Ala Glu Gly Gln Lys Gln Gly Gln Leu Arg Ser Leu His Leu Thr Cys
            835                 840                 845

Cys Ser Ala Pro Val Gly Ser Gln Gly Thr Trp Ser Thr Ser Cys Arg
850                 855                 860

Ile Asn His Leu Ile Phe Arg Gly Gly Ala Gln Ile Thr Phe Leu Ala
865                 870                 875                 880

Thr Phe Asp Val Ser Pro Lys Ala Val Gly Leu Asp Arg Leu Leu Leu
            885                 890                 895

Ile Ala Asn Val Ser Ser Glu Asn Asn Ile Pro Arg Thr Ser Lys Thr
            900                 905                 910

Ile Phe Gln Leu Glu Leu Pro Val Lys Tyr Ala Val Tyr Ile Val Val
            915                 920                 925

Ser Ser His Glu Gln Phe Thr Lys Tyr Leu Asn Phe Ser Glu Ser Glu
            930                 935                 940

Glu Lys Glu Ser His Val Ala Met His Arg Tyr Gln Val Asn Asn Leu
945                 950                 955                 960

Gly Gln Arg Asp Leu Pro Val Ser Ile Asn Phe Trp Val Pro Val Glu
                965                 970                 975

Leu Asn Gln Glu Ala Val Trp Met Asp Val Glu Val Ser His Pro Gln
            980                 985                 990

Asn Pro Ser Leu Arg Cys Ser Ser Glu Lys Ile Ala Pro Pro Ala Ser
            995                 1000                1005

Asp Phe Leu Ala His Ile Gln Lys Asn Pro Val Leu Asp Cys Ser Ile
    1010                1015                1020

Ala Gly Cys Leu Arg Phe Arg Cys Asp Val Pro Ser Phe Ser Val Gln
1025                1030                1035                1040

Glu Glu Leu Asp Phe Thr Leu Lys Gly Asn Leu Ser Phe Gly Trp Val
                1045                1050                1055

Arg Gln Ile Leu Gln Lys Lys Val Ser Val Val Ser Val Ala Glu Ile
            1060                1065                1070

Ile Phe Asp Thr Ser Val Tyr Ser Gln Leu Pro Gly Gln Glu Ala Phe
            1075                1080                1085
```

```
         Met  Arg  Ala  Gln  Thr  Ile  Thr  Val  Leu  Glu  Lys  Tyr  Lys  Val  His  Asn
              1090                1095                1100

Pro  Ile  Pro  Leu  Ile  Val  Gly  Ser  Ser  Ile  Gly  Gly  Leu  Leu  Leu  Leu
         1105                1110                     1115                          1120

Ala  Leu  Ile  Thr  Ala  Val  Leu  Tyr  Lys  Val  Gly  Phe  Phe  Lys  Arg  Gln
                        1125                          1130                     1135

Tyr  Lys  Glu  Met  Met  Glu  Glu  Ala  Asn  Gly  Gln  Ile  Ala  Pro  Glu  Asn
                        1140                     1145                     1150

Gly  Thr  Gln  Thr  Pro  Ser  Pro  Pro  Ser  Glu  Lys
                        1155                1160
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
         Phe  Asn  Leu  Asp  Val  Glu  Glu  Pro  Met  Val  Phe  Gln
         1                   5                        10
```

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TTYAAYYTGG AYGTNGARGA RCCNATGGTN TTYCA                                       3 5

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TTCAACCTGG ACGTGGAGGA GCCCATGGTG TTCCAA                                      3 6

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TTCAACCTGG ACGTNGAASA NCCCATGGTC TTCCAA                                      3 6

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single (D) TOPOLOGY: linear (ii) MOLECULE TYPE: DNA (xi) SEQUENCE DESCRIPTION: SEQ ID NO:9:

TTYAAYYTNG AYGTNGARGA RCC 23

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

TTYAAYYTGG ACGTNGAAGA 20

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

TGRAANACCA TNGGYTC 17

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TTGGAAGACC ATNGGYTC 18

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

ATTAACCCTC ACTAAAG 17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

AATACGACTC ACTATAG 17

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Val Phe Gln Glu Xaa Gly Ala Gly Phe Gly Gln
1               5                   10
```

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Leu Tyr Asp Xaa Val Ala Ala Thr Gly Leu Xaa Gln Pro Ile
1               5                   10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Pro Leu Glu Tyr Xaa Asp Val Ile Pro Gln Ala Glu
1               5                   10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Phe Gln Glu Gly Phe Ser Xaa Val Leu Xaa
1               5                   10
```

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Thr Ser Pro Thr Phe Ile Xaa Met Ser Gln Glu Asn Val Asp
1               5                   10
```

( 2 ) INFORMATION FOR SEQ ID NO:20:

( i ) SEQUENCE CHARACTERISTICS:
        ( A ) LENGTH: 17 amino acids
        ( B ) TYPE: amino acid ( D ) TOPOLOGY: linear ( i i ) MOLECULE TYPE: peptide ( x i ) SEQUENCE DESCRIPTION: SEQ ID NO:20:

Leu Val Val Gly Ala Pro Leu Glu Val Val Ala Val Xaa Gln Thr Gly
1               5                       10                      15

Arg ( 2 ) INFORMATION FOR SEQ ID NO:21:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:21:

Leu Asp Xaa Lys Pro Xaa Asp Thr Ala
1               5

( 2 ) INFORMATION FOR SEQ ID NO:22:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

Phe Gly Glu Gln Phe Ser Glu
1               5

( 2 ) INFORMATION FOR SEQ ID NO:23:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:23:

RAANCCYTCY TGRAAACTYT C                                      21

( 2 ) INFORMATION FOR SEQ ID NO:24:

( i ) SEQUENCE CHARACTERISTICS:
      ( A ) LENGTH: 1006 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:24:

TTCAACCTGG ACGTGGAGGA GCCCATGGTG TTCAAGAGGA TGGAGCTGGC TTTGGACAGA    60

GCGTGGCCCA GCTTGGCGGA TCTAGACTCG TGGTGGGAGC CCCCCTGGAG GTGGTGGCGG   120

TCAACCAAAC AGGAAGGTTG TATGACTGTG TGGCTGCCAC TGGCCTTGTC AACCCATACC   180

CCTGCACACA CCCCCAGATG CTGTGAACAT GTCCCTGGGT CTGTCCCTGT CAGCCGCCGC   240

CAGTCGCCCC TGGCTGCTGG CCTGTGGCCC AACCATGCAC AGAGCCTGTG GGGAGAATAT   300

GTATGCAGAA GGCTTTTGCC TCCTGTTGGA CTCCATCTG CAGACCATTT GGACAGTACC    360

| | | | | | |
|---|---|---|---|---|---|
|TGCTGCCCTA|CCAGAGTGTC|CAAGTCAAGA|GATGGACATT|GTCTTCCTGA|TTGATGGTTC|420|
|TGGCAGTATG|AGCAAAGTGA|CTTTAAACAA|ATGAAGGATT|TGTGAGAGCT|GTGATGGGAC|480|
|AGTTTGAGGG|CACCCAAACC|CTGTTCTCAC|TGATACAGTA|TCCCACCTCC|CTGAAGATCC|540|
|ACTTCACCTT|CACGCAATTC|CAGAGCAGCT|GGAACCCTCT|GAGCCTGGTG|GATCCCATTG|600|
|TCCAACTGGA|CGGCCTGACA|TATACAGCCA|CGGGCATCCG|GAAAGTGGTG|GAGGAACTGT|660|
|TTCATAGTAA|GAATGGGGCC|CGTAAAAGTG|CCAAGAAGAT|CCTCATTGTC|ATCACAGATG|720|
|GCAAAATAC|AAAGACCCCC|TGGAGTACGA|GGACGTATCC|CCAGGCAGAG|AGAGCGGATC|780|
|ATCCGCTATG|CCATTGGGGT|GGGAGATGCT|TTCTGGAAAC|CCAGTGCCAA|GCAGGAGCTG|840|
|GACAACATTG|GCTCAGAGCC|GGCTCAGGAC|CATGTGTTCA|GGGTGGACAA|CTTTGCAGCA|900|
|CTCAGCAGCA|TCCAGGAGCA|GCTGCAGGAG|AAGATCTTTG|CACTCGAAGG|AACCCAGTCG|960|
|ACGACAAGTA|GCTCTTTCCA|ACATGAGATG|TTCCAAGAAG|GGTTCA| |1006|

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTNTTYCARG ARGAYGG                                 17

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CCACTGTCAG GATGCCCGTG                             20

( 2 ) INFORMATION FOR SEQ ID NO:27:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

AGTTACGAAT TCGCCACCAT GGCTCTACGG GTGCTTCTTC TG          42

( 2 ) INFORMATION FOR SEQ ID NO:28:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

AGTTACGAAT TCGCCACCAT GACTCGGACT GTGCTTCTTC TG          42

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

AGTTACGAAT TCGCCACCAT GACCTTCGGC ACTGTG     36